(12) United States Patent
Greene et al.

(10) Patent No.: US 6,403,557 B1
(45) Date of Patent: *Jun. 11, 2002

(54) FIBROBLAST GROWTH FACTOR-13

(75) Inventors: John M. Greene, Gaithersburg, MD (US); Joachim R. Gruber, Dallas, TX (US); Craig A. Rosen, Laytonsville, MD (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/976,315

(22) Filed: Nov. 21, 1997

Related U.S. Application Data

(63) Continuation-in-part of application No. 08/462,965, filed as application No. PCT/US95/07108 on Jun. 5, 1995, now Pat. No. 5,728,546.
(60) Provisional application No. 60/031,969, filed on Nov. 27, 1996, and provisional application No. 60/031,575, filed on Dec. 4, 1996.

(51) Int. Cl.$^7$ .......................... A61K 38/18; C07K 14/50
(52) U.S. Cl. .......................... 514/12; 530/350; 530/399; 514/2
(58) Field of Search ................................ 530/350, 399; 435/69.1, 69.4; 514/2, 12

(56) References Cited

U.S. PATENT DOCUMENTS

| | | | | |
|---|---|---|---|---|
| 5,728,546 A | * | 3/1998 | Greene et al. | |
| 5,773,252 A | * | 6/1998 | Greene et al. | |

FOREIGN PATENT DOCUMENTS

| | | |
|---|---|---|
| JP | 05-222096 | 8/1993 |
| TW | 264481 A | 12/1995 |
| WO | WO 95/03831 | 2/1995 |
| WO | WO 95/14772 | 6/1995 |
| WO | WO 95/24928 | 9/1995 |
| WO | WO 96/39508 | 12/1996 |
| WO | WO 96/39509 | 12/1996 |
| WO | WO 97/44468 | 11/1997 |
| WO | WO 98/08864 | 3/1998 |
| WO | WO 98/16644 | 4/1998 |
| WO | 98/23749 | 6/1998 |
| WO | WO 99/14327 | 3/1999 |
| WO | WO 99/14328 | 3/1999 |

OTHER PUBLICATIONS

Supplementary European Search Report, Application No. EP 95 92 2214 (Mar. 31, 1998).
International Search Report, Application No. PCT/US 97/20548 (Apr. 21, 1998).
International Search Report, Application No. PCT/US95/07156 (Sep. 11, 1995).
Ataliotis et al. (1997) Int. Rev. Cytol. 172:95–127.
Crossley et al. (1996) Cell 84(1):127–136.
Galzie et al. (1997) Biochem Cell Biol. 75(6):669–685.
Ghosh et al. (1996) Cell Growth & Differ. 7(10):1425–1434.
Gospodarowicz, D. (1991) Cell Biol. Rev. 25(4):307–314.
Hartung et al. (1997) Mech. Development 64(1/2):31–39.
Kirsch et al. (1997) J. of Neuro. Onco. 35(3):289–301.
Klagsbrunn et al. (1998) Progress in Growth Factor Research 1:207–235.
Linnekin et al. (1997) Leuk. Lymphoma 27(5–6):439–444.
Mason, I.J. (1994) Cell 78:547–552.
Payson et al. (1996) Oncogene 13(1):47–53.
Smallwood et al. (1996) PNAS USA 93:9850–9857.
Szebenyi et al. (1999) Int. Rev. Cytol. 185:45–106.
Tanaka et al. (1995) FEBS Lett. 363(3):226–230.
Tanaka et al. (1992) PNAS USA 89(19):8928–8932.
Vogel et al. (1996) Development 122(6):1737–1750.
Yao et al. (1997) Soc. for Neuroscience Abstracts 23(1–2):2439.
Vlodavsky, et al., 1989, *Annals NY Academy of Sciences*. vol. 638: 207–220.
Terada et al., 1991, Origins of Human Cancer. vol. 404: 675–683.
International Search Report, Appl. No. PCT/US00/40080, dated Dec. 28, 2000.

* cited by examiner

*Primary Examiner*—Marianne P. Allen
(74) *Attorney, Agent, or Firm*—Human Genome Sciences, INC

(57) ABSTRACT

The present invention relates to a novel FGF-13 protein which is a member of the fibroblast growth factor (FGF) family. In particular, isolated nucleic acid molecules are provided encoding the human FGF-13 protein. FGF-13 polypeptides are also provided as are vectors, host cells and recombinant methods for producing the same. The invention further relates to screening methods for identifying agonists and antagonists of FGF-13 activity. Also provided are diagnostic methods for detecting FGF-13-related disorders and therapeutic methods for treating FGF-13-related disorders. Disclosed is a method of prolonging dopaminergic neuron survival.

50 Claims, 17 Drawing Sheets

```
  1 ATGGGAGCCGCCCGCCTGCTGCCCAACCTCACTCTGTGCTTGCTTACAGCTGCTGATTCTCTGC  60
  1  M  G  A  A  R  L  L  P  N  L  T  L  C  L  L  Q  L  L  I  L  C   20

61 TGTCAAACTCAGGGGAGAATCACCCCGTCTCTCCTAATTTTAACCAGTACGTGAGGGACCAG  120
 21  C  Q  T  Q  G  E  N  H  P  S  P  N  F  N  Q  Y  V  R  D  Q    40

121 GGCCGCCATGACCGACCAGCTGAGCAGGCGGCAGATCCGCGAGTACCAACTCTACAGCAGG  180
 41  G  A  M  T  D  Q  L  S  R  R  Q  I  R  E  Y  Q  L  Y  S  R    60

181 ACCAGTGGCAAGCACGTGCAGGTCACCGGTCGCCATCTCCGCCACCCGCCGAGGACGGC  240
 61  T  S  G  K  H  V  Q  V  T  G  R  I  S  A  T  A  E  D  G    80

241 AACAAGTTTGCCAAGCTCATAGTGGAGACGGACACGTTTGGCAGCCGGGTTCGCATCAAA  300
 81  N  K  F  A  K  L  I  V  E  T  D  T  F  G  S  R  V  R  I  K   100
```

FIG. 1A

```
301 GGGGCTGAGAGTGAGAAGTACATCTGTATGAACAAGAGGGCAAGCTCATCGGGAAGCCC 360
101  G   A   E   S   E   K   Y   I   C   M   N   K   R   G   K   L   I   G   K   P  120

361 AGCGGGAAAGAGCAAAGACTGCGTGTTCACGGAGATCGTGCTGGAGAACAACTATACGGCC 420
121  S   G   K   E   Q   R   L   R   V   F   T   E   I   V   L   E   N   N   Y   T   A  140

421 TTCCAGAACGCCCGGCACGAGGGCTGGTTCATGGCCCTTCACGCCTTCATCAAGCGCCCGC 480
141  F   Q   N   A   R   H   E   G   W   F   M   A   F   T   R   Q   R   P   R  160

481 CAGGCTTCCCCGCAGAACCAGCGCGAGGCCCACTTCATCAAGCGCCTCTACCAA 540
161  Q   A   S   R   Q   N   Q   R   E   A   H   F   I   K   R   L   Y   Q  180

541 GGCCAGCTGCCCTTCCCCAACCACGCCGAGAAGCAGAAGCAGTTCGAGTTTGTGGGCTCC 600
181  G   Q   L   P   F   P   N   H   A   E   K   Q   K   Q   F   E   F   V   G   S  200
```

FIG. 1B

601 GCCCCCACCCGCCCGGACCAAGCCACACGGCCGGCCCCCAGCCCCTCACGTAGTCTGGGAGG 660
201  A  P  T  R  R  T  K  R  T  R  R  P  Q  P  L  T  *                216

661 CAGGGGGCAGCAGCCCCTGGGCCGCCTCCCCACCCCTTCTTAATCCAAGGACTG 720

721 GGCTGGGGTGGCGGGAGGGGAGCCAGATCCCGAGGAGGACCCTGAGGGCCGAAGCA 780

781 TCCGAGCCCCCAGCTGGGAAGGGGCAGGCCCAGGGGCCGGTGCCCCGGCTGGCACAGTGCCC 840

841 CCTTCCCCGGACGGGTGGCAGGCCCAGCCCCTGGAGAGGAACTGAGTGTCACCCTGATCTTCAGGCCA 900

901 CCAGCCCCTCTGCCCAGCCCCTCCCCAGCCCTGAAGCCCGGCTCCTGAAAAGGTCAGCGACTGAA 960

961 GGCCCTTGCAGACAACCGTCTGGAGGTGGCTGTCCCTCAAAATCTGCTTCCTCCGGATCTCCCCT 1020

FIG. 1C

1021 CAGTCTGCCCCCCAGCCCCCAAAACTCCTCCCTGGCTAGACTGTAGGAAGGGACTTTTGTTTG 1080

1081 TTTGTTTGTTTCAGGAAAAAAGAAAAGGGAGAGAGAGGAAAAATAGAGGGTTGTCCACTCCT 1140

1141 CACATTCCACGACCCCAGGCCCTGCACCCCCACCCCCAACTCCCCAGCCCCCGGAATAAAAACCAT 1200

1201 TTTCCTGCA 1209

```
        1                                                                               80
aFGF    MA......EGEIT................TFTALT................EKFN...L..PPG..............
bFGF    MA......AGSIT................TLPALP................EDGGSGAF..PPG..............
Int-2   MG......LIWLL................LLSLLEPGWPAAGPGARLR...RDAGGRGGVYEHLG..............
FGF4    MS..........GPGTAAVALLPAVL.LALLAPWA......GRGGAAAPTAPNGTLEAEL..ERRWESLVALSLARLPV
FGF5    MSLSFLLLLFFSH...............LILSAWAHGEKRLAPKGQPGPAATDRNPRGSSSRQSSSSAMSSSSASSSPA
FGF6    MALGQKLFITMSRGAGRLQGTLWALVF.LGILV...........GMVVPSPAGTRANNTLLDSRGWGTL....LSRSRA
KGF     MH...KWILTWILPTLLYRSCFHIICL.VGTISLACNDMTPEQMATNVNCSSPERHTRSYDYMEGG..............
FGF8    M...........GSPR...SALSCLLLHLLVLCLQAQV..............TVQSSPNFTQHVREQSLVTDQLSRRLI
FGF13   M...........GAARLLPNLT.LCLQLLILLCQTQG..............ENHPSPNFNQYVRDQGAMTDQLSRRQI 81                                                                              160
aFGF    ....................NYKKPKLLYCSNG.GHFLRILPDGTVDGTRDRSDQHIQLQLSAESVGE.VYIKSTETGQYL
bFGF    ....................HFKDPKRLYCKNG.GFFLRIHPDGRVDGVREKSDPHIKLQLQAEERGV.V3IKGVCANRYL
Int-2   ....................GAPRRRKLYCATK..YHLQLHPSGRVNGSLENSAYSI.LEITAVEVGI.VAIRGLFSGRYL
FGF4    A.AQPKEAAVQSGAGDYLLGIKRLRRLYCNVGIGFHLQALPDGRIGGAHA.DTRDSLLELSPVERGV.VSIFGVASRFFV
FGF5    ASLGSQGSGLEQSSFQWSLGA.RTGSLYCRVGIGFHLQIYPDGKVNGSHE.ANMLSVLEIFAVSQGI.VGIRGVFSNKFL
FGF6    G.LAGEIAGVNWESG.YLVGIKRQRRLYCNVGIGFHLQVLPDGRISGTHE.ENPYSLLEISTVERGV.VSLFGVRSALFV
KGF     ....................DI.RVRRLFCRTQ..WYLRIDKRGKVKGTQEMKNNYNIMEIRTVAVGI.VAIKGVESEFYL
FGF8    ....................RTYQLYSRTS.GKHVQVLANKRINAMAEDGDPFAKLIVETDTFGSRVRVRGAETGLYI
FGF13   ....................REYQLYSRTS.GKHVQV.TGRRISATAEDGNKFAKLIVETDTFGSRVRIKGAESEKYI 161                                                                             240
aFGF    AMDTDGLLYGSQTPNE.ECLFLERLEENHYNTYISKKH..............AEKNWFVGLKKNGSCKRG..PRTHYGQK
bFGF    AMKEDGRLLASKCVTD.ECFFFERLESNNYNTYRSRKY.............T..SWYVALKRTGQYKLG..SKTGPGQK
Int-2   AMNKRGRLYASEHYSA.ECEFVERIHELGYNTYASRLYRTVSSTPGARRQPSAERLWYVSVNGKGRPRRG..FKTRRTQK
FGF4    AMSSKGKLYGSPFFTD.ECTFKEILLPNNYNAYESYKYPGM...............PIALSKNGKTKKG..NRVSPTMK
FGF5    AMSKKGKLHASAKFTD.DCKFRERFQENSYNTYASAIHRTEK.........TGREWYVALNKRGKAKRGCSPRVKPQHI
FGF6    AMNSKGRLYATPSFQE.ECKFRETLLPNNYNAYESDLYQGT..............YIALSKYGRVKG..SKVSPIMT
KGF     AMNKEGKLYAKKECNE.DCNFKELILENHYNTYASAK........WTHNGGEM..FVALNQKGIPVRG..KKTKKEQK
FGF8    CMNKKGKLIAKSNGKGKDCVFTEIVLENNYTALQNAKYEG.............WYMAFTRKGRPRKG..SKTRQHQR
FGF13   CMNKRGKLIGKPSGKSKDCVFTEIVLENNYTAFQNARHEG.............WFMAFTRQGRPRQA..SRSRQNQR 241                                                                             305
aFGF    AILFLP.............................................LPVSSD
bFGF    AILFLP.............................................MSAKS.
Int-2   SSLFLPRVLDHRDHEMVRQLQSGLPRPPGKGVQPRRRRQKQSPDNLEPSHVQASRLGSQLEASAH
FGF4    VTHFLPRL............................................
FGF5    STHFLPRFKQSEQPELSFTVTVPEKKNPPSPIKSKIP........LSAPRKNTNSVKYRLKFRFG
FGF6    VTHFLPRI.............................................
KGF     TAHFLPMAIT...........................................
FGF8    EVHFMKRL..........PRGH....HTTEQSLRFEFLNYPPFTRSLRGSQRTWAP.....EP..R
FGF13   EAHFIKRL..........YQGQLPFPNHAEKQKQFEFVGSAPTRRT....KRTRRP.....QPLT.
```

FIBROBLAST GROWTH FACTOR-13

This application is a continuation-in-part of, and claims the benefit of priority under 35 U.S.C. §120 to U.S. application Ser. No. 08/462,965, filed Jun. 5, 1995, now issued as U.S. Pat. No. 5,728,546 and PCT Application No. PCT/US095/07108, filed Jun. 5, 1995. This application also claims the benefit of priority under 35 U.S.C. §119(e) of U.S. Provisional Application Ser. Nos. 60/031,969 and 60/031,575, filed Nov. 27, 1996 and Dec. 4, 1996, respectively.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention have been putatively identified as fibroblast growth factor/heparin binding growth factor, hereinafter referred to as Fibroblast Growth Factor-13 (hereafter, "FGF-13"). The invention also relates to inhibiting the action of such polypeptides.

BACKGROUND OF THE INVENTION

Fibroblast growth factors are a family of proteins characteristic of binding to heparin and are, therefore, also called heparin binding growth factors (HBGF). Expression of different members of these proteins are found in various tissues and are under particular temporal and spatial control. These proteins are potent mitogens for a variety of cells of mesodermal, ectodermal, and endodermal origin, including fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells.

Each member has functions overlapping with others and also has its unique spectrum of functions. In addition to the ability to stimulate proliferation of vascular endothelial cells, both FGF-1 and 2 are chemotactic for endothelial cells and FGF-2 has been shown to enable endothelial cells to penetrate the basement membrane. Consistent with these properties, both FGF-1 and 2 have the capacity to stimulate angiogenesis. Another important feature of these growth factors is their ability to promote wound healing. Many other members of the FGF family share similar activities with FGF-1 and 2 such as promoting angiogenesis and wound healing. Several members of the FGF family have been shown to induce mesoderm formation and to modulate differentiation of neuronal cells, adipocytes and skeletal muscle cells.

Other than these biological activities in normal tissues, FGF proteins have been implicated in promoting tumorigenesis in carcinomas and sarcomas by promoting tumor vascularization and as transforming proteins when their expression is deregulated.

The FGF family presently consists of eight structurally-related polypeptides: basic FGF, acidic FGF, int 2, hst 1/k-FGF, FGF-5, FGF-6, keratinocyte growth factor, AIGF (FGF-8); and recently a glia-activating factor has been shown to be a novel heparin-binding growth factor which was purified from the culture supernatant of a human glioma cell line (Miyamoto, M. et al., *Mol. and Cell. Biol.*, 13(7) :4251–4259 (1993). The genes for each have been cloned and sequenced. Two of the members, FGF-1 and FGF-2, have been characterized under many names, but most often as acidic and basic fibroblast growth factor, respectively. The normal gene products influence the general proliferation capacity of the majority of mesoderm and neuroectoderm-derived cells. They are capable of inducing angiogenesis in vivo and may play important roles in early development (Burgess, W. H. and Maciag, T., *Ann. Rev. Biochem.*, 58:575–606 (1989)).

Many of the above-identified members of the FGF family also bind to the same receptors and elicit a second message through binding to these receptors.

A eukaryotic expression vector encoding a secreted form of FGF-1 has been introduced by gene transfer into porcine arteries. This model defines gene function in the arterial wall in vivo. FGF-1 expression induced intimal thickening in porcine arteries 21 days after gene transfer (Nabel, E. G., et al., *Nature*, 362:844–6 (1993)). It has further been demonstrated that basic fibroblast growth factor may regulate glioma growth and progression independent of its role in tumor angiogenesis and that basic fibroblast growth factor release or secretion may be required for these actions (Morrison, R. S., et al., *J. Neurosci. Res.* 34:502–509 (1993)).

Fibroblast growth factors, such as basic FGF, have further been implicated in the growth of Kaposi's sarcoma cells in vitro (Huang, Y. Q., et al., *J. Clin. Invest.* 91:1191–1197 (1993)). Also, the cDNA sequence encoding human basic fibroblast growth factor has been cloned downstream of a transcription promoter recognized by the bacteriophage T7 RNA polymerase. Basic fibroblast growth factors so obtained have been shown to have biological activity indistinguishable from human placental fibroblast growth factor in mitogenicity, synthesis of plasminogen activator and angiogenesis assays (Squires, C. H., et al., *J. Biol. Chem.* 263:16297–16302 (1988)).

U.S. Pat. No. 5,155,214 discloses substantially pure mammalian basic fibroblast growth factors and their production. The amino acid sequences of bovine and human basic fibroblast growth factor are disclosed, as well as the DNA sequence encoding the polypeptide of the bovine species.

Newly discovered FGF-9 has around 30% sequence similarity to other members of the FGF family. Two cysteine residues and other consensus sequences in family members were also well conserved in the FGF-9 sequence. FGF-9 was found to have no typical signal sequence in its N terminus like those in acidic and basic FGF. However, FGF-9 was found to be secreted from cells after synthesis despite its lack of a typical signal sequence FGF (Miyamoto, M. et al., *Mol. and Cell. Biol.* 13(7):4251–4259 (1993). Further, FGF-9 was found to stimulate the cell growth of oligodendrocyte type 2 astrocyte progenitor cells, BALB/c 3T3, and PC-12 cells but not that of human umbilical vein endothelial cells (Naruo, K., et al., *J. Biol. Chem.* 268:2857–2864 (1993).

Basic FGF and acidic FGF are potent modulators of cell proliferation, cell motility, differentiation, and survival and act on cell types from ectoderm, mesoderm and endoderm. These two FGFs, along with KGF and AIGF, were identified by protein purification. However, the other four members were isolated as oncogenes, expression of which was restricted to embryogenesis and certain types of cancers. FGF-9 was demonstrated to be a mitogen against glial cells. Members of the FGF family are reported to have oncogenic potency. FGF-9 has shown transforming potency when transformed into BALB/c 3T3 cells (Miyamoto, M., et al., *Mol. Cell. Biol.* 13(7):4251–4259 (1993).

Androgen induced growth factor (AIGF), also known as FGF-8, was purified from a conditioned medium of mouse mammary carcinoma cells (SC-3) simulated with testosterone. AIGF is a distinctive FGF-like growth factor, having a putative signal peptide and sharing 30–40% homology with known members of the FGF family. Mammalian cells transformed with AIGF shows a remarkable stimulatory effect on the growth of SC-3 cells in the absence of androgen. Therefore, AIGF mediates androgen-induced growth of SC-3 cells, and perhaps other cells, since it is secreted by the tumor cells themselves.

SUMMARY OF THE INVENTION

The polypeptide of the present invention has been putatively identified as a member of the FGF family as a result of amino acid sequence homology with other members of the FGF family.

In accordance with one aspect of the present invention, there are provided novel mature polypeptides as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides of the present invention, including mRNAs, DNAs, cDNAs, genomic DNA, as well as antisense analogs thereof and biologically active and diagnostically or therapeutically useful fragments thereof.

Thus, the present invention provides -isolated nucleic acid molecules comprising a polynucleotide encoding at least a portion of the FGF-13 polypeptide having the complete amino acid sequence shown in SEQ ID NO:2 or the complete amino acid sequence encoded by the cDNA clone deposited as plasmid DNA in a bacterial host as ATCC Deposit Number 97148 on May 12, 1995. The nucleotide sequence determined by sequencing the deposited FGF-13 clone, which is shown in FIGS. 1A–D (SEQ ID NO:1), contains an open reading frame encoding a complete polypeptide of 216 amino acid residues, including an initiation codon encoding an N-terminal methionine at nucleotide positions 1 to 3. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC Deposit Number 97148, which molecules also can encode additional amino acids fused to the N-terminus of the FGF-13 amino acid sequence.

Accordingly, one aspect of the invention provides an isolated nucleic acid molecule comprising a polynucleotide comprising a nucleotide sequence selected from the group consisting of: (a) a nucleotide sequence encoding the FGF-13 polypeptide having the complete amino acid sequence in SEQ ID NO:2 excepting the N-terminal methionine (i.e., positions -22 to 193 of SEQ ID NO:2); (b) a nucleotide sequence encoding the predicted mature FGF-13 polypeptide having the amino acid sequence from about position 1 to about position 193 in SEQ ID NO:2; (c) a nucleotide sequence encoding the FGF-13 polypeptide having the complete amino acid sequence encoded by the cDNA clone contained in ATCC Deposit No. 97148; and (d) a nucleotide sequence encoding the mature FGF-13 polypeptide having the amino acid sequence encoded by the cDNA clone contained in ATCC Deposit No. 97148; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of an FGF-13 polypeptide having an amino acid sequence in (a), (b), (c) or (d), above.

In accordance with still another aspect of the present invention, there are provided processes for producing such polypeptides by recombinant techniques through the use of recombinant vectors, such as cloning and expression plasmids useful as reagents in the recombinant production of the polypeptides of the present invention, as well as recombinant prokaryotic and/or eukaryotic host cells comprising a nucleic acid sequence encoding a polypeptide of the present invention.

In accordance with a further aspect of the present invention, there is provided a process for utilizing such polypeptides, or polynucleotides encoding such polypeptides, for screening for agonists and antagonists thereto and for therapeutic purposes, for example, promoting wound healing for example as a result of burns and ulcers, to prevent neuronal damage associated with stroke and due to neuronal disorders and promote neuronal growth for example Parkinson's disease, and to prevent skin aging and hair loss, to stimulate angiogenesis, mesodermal induction in early embryos and limb regeneration.

In accordance with yet a further aspect of the present invention, there are provided antibodies against such polypeptides.

In accordance with yet another aspect of the present invention, there are provided antagonists against such polypeptides and processes for their use to inhibit the action of such polypeptides, for example, in the treatment of cellular transformation, for example, tumors, to reduce scarring and treat hyper-vascular diseases.

In accordance with another aspect of the present invention, there are provided nucleic acid probes comprising nucleic acid molecules of sufficient length to specifically hybridize to a polynucleotide encoding a polypeptide of the present invention.

In another embodiment, the invention provides an isolated antibody that binds specifically to an FGF-13 polypeptide having an amino acid sequence described in (a), (b), (c) or (d) above. The invention further provides methods for isolating antibodies that bind specifically to an FGF-13 polypeptide having an amino acid sequence as described herein. Such antibodies are useful diagnostically or therapeutically as described below.

In accordance with yet another aspect of the present invention, there are provided diagnostic assays for detecting diseases or susceptibility to diseases related to mutations in a nucleic acid sequence of the present invention and for detecting over-expression or under-expression of the polypeptides encoded by such sequences.

In accordance with another aspect of the present invention, there is provided a process for utilizing such polypeptides, or polynucleotides encoding such polypeptides, for in vitro purposes related to scientific research, synthesis of DNA and manufacture of DNA vectors. Thus, the invention also provides pharmaceutical compositions comprising FGF-13 polypeptides, particularly human FGF-13 polypeptides. Methods of treating individuals in need of FGF-13 polypeptides are also provided. The invention further provides compositions comprising an FGF-13 polynucleotide or an FGF-13 polypeptide for administration to cells in vitro, to cells ex vivo and to cells in vivo, or to a multicellular organism. In certain particularly preferred embodiments of this aspect of the invention, the compositions comprise an FGF-13 polynucleotide for expression of an FGF-13 polypeptide in a host organism for treatment of disease. Particularly preferred in this regard is expression in a human patient for treatment of a dysfunction associated with aberrant endogenous activity of an FGF-13 gene.

BRIEF DESCRIPTION OF THE FIGURES

The following drawings are meant only as illustrations of specific embodiments of the present invention and are not meant as limitations in any manner.

FIGS. 1A–D depicts the nucleotide sequence (SEQ ID NO:1) of the human mRNA encoding FGF-13 and the deduced amino acid sequence (SEQ ID NO:2) of the FGF-13 polypeptide. The putative leader sequence of about 23 amino acids is underlined. Note that the methionine residue at the beginning of the leader sequence in FIGS. 1A–D is shown in position number (positive) 1, whereas the leader positions in the corresponding sequence of SEQ ID NO:2 are designated with negative position numbers. Thus, the leader sequence positions 1 to 23 in FIGS. 1A–D correspond to positions −23 to −1 in SEQ ID NO:2.

FIG. 2 shows an alignment of the regions of identity among the amino acid sequences of the human FGF-13 protein and the amino acid sequences of the following human proteins: acidic FGF (SEQ ID NO:3), basic FGF (SEQ ID NO:4), Int-2 (SEQ ID NO:5), FGF-4 (SEQ ID NO:6), FGF-5 (SEQ ID NO:7), FGF-6 (SEQ ID NO:8), Keratinocyte Growth Factor (KGF) (SEQ ID NO:9), and AIGF (FGF-8) (SEQ ID NO:10), as determined by the "Megalign" routine of the DNAStar program.

DETAILED DESCRIPTION

Figure 3:
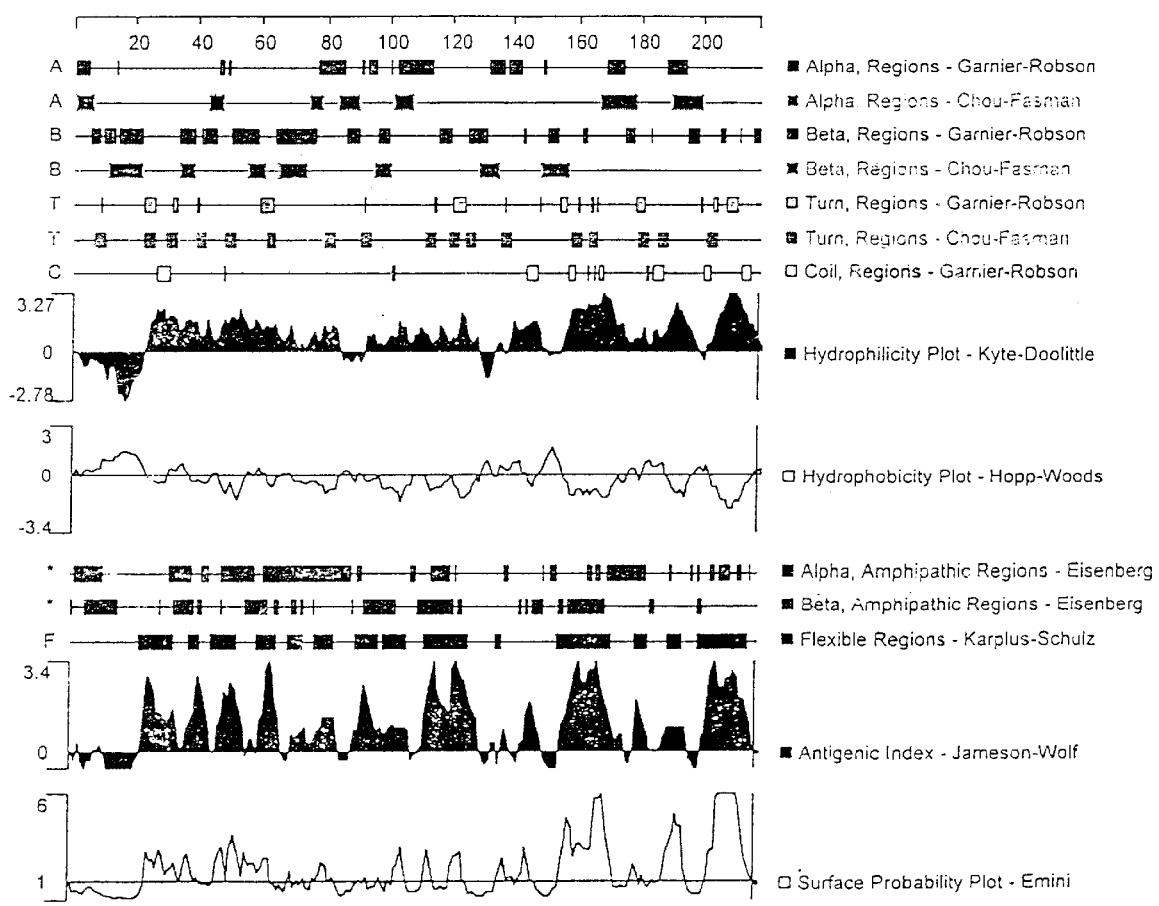
FIG. 3 shows an analysis of the FGF-13 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the indicate location of the highly antigenic regions of the FGF-13 protein, i.e., regions from which epitope-bearing peptides of the invention may be obtained.

The present invention provides isolated nucleic acid molecules comprising a polynucleotide encoding an FGF-13 polypeptide having the amino acid sequence shown in SEQ ID NO:2, which was determined by sequencing cloned cDNAs. The nucleotide sequence shown in positions 11–1212 of SEQ ID NO:1 was obtained by sequencing the HODAH63 clone, which was deposited on May 12, 1995 at the American Type Culture Collection, 10801 University Boulevard, Manassas, Va. 20110-2209, and given accession number ATCC 97148. The deposited clone is contained in the pBluescript SK(–) plasmid (Stratagene, La Jolla, Calif.). The nucleotide sequence shown in positions 1–10 of SEQ ID NO:1 was obtained by sequencing the product of a PCR amplification of a cDNA library containing a mixture of human cDNAs.

The deposit referred to herein will be maintained under the Budapest Treaty on the International Recognition of the Deposit of Microorganisms for the purposes of Patent Procedure. This deposit is provided merely as a convenience and is not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The FGF-13 polypeptide is structurally related to all members of the fibroblast growth factor family and contains an open reading frame encoding a polypeptide of 216 amino acids (SEQ ID NO:2) of which the first 23 amino acids represent a putative leader sequence such that the mature polypeptide comprises 193 amino acids. Among the top matches are:

1) 69% identity and 81% similarity to mouse AIGF over a stretch of 185 amino acids; 2) 30% identity and 56% similarity with FGF-4 from in a region of 82 amino acids; 3) 41% identity and 64% similarity with human KGF (SEQ ID NO:9) over a stretch of 78 amino acids. Among human homologs compared to FGF-13, FGF-8 (bFGF) and aFGF show the greatest similarities (56.7% and 51.0%, respectively). An alignment of the FGF-13 amino acid sequence with the amino acids sequences of various human polypeptides is shown in FIG. 2.

The FGF/HBGF family signature, GXLX(S, T, A, G)X6 (D, E)CXFXE (SEQ ID NO:38), is conserved in the polypeptide of the present invention (X means any amino acid residue; (D, E) means either D or E residue; X6 means any 6 amino acid residues).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A–D (SEQ ID NO:1), a nucleic acid molecule of the present invention encoding an FGF-13 polypeptide may be obtained using standard cloning and screening procedures, such as those for cloning cDNAs using mRNA as starting material. Illustrative of the invention, the nucleic acid molecule described in FIGS. 1A–D (SEQ ID NO:1) was discovered in a cDNA library derived from human ovarian cancer tissue. Additional clones of the same gene were also identified in cDNA libraries from human fetal kidney tissue, and Northern blotting of human tissues detected a weak signal (1.6 kb) only in human fetal kidney and human fetal brain. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of tissue(s) or cell type(s).

The determined nucleotide sequence of the FGF-13 cDNA of FIGS. 1A–D (SEQ ID NO:1) contains an open reading frame encoding a protein of 216 amino acid residues, with an initiation codon at nucleotide positions 1 to 3 of the nucleotide sequence in FIGS. 1A–D (SEQ ID NO:1). The FGF-13 polypeptide encoded by the deposited cDNA actually comprises about the 212 amino acids at the C-terminal end of the sequence in SEQ ID NO:2, with the remaining N-terminal sequences in FIGS. 1A–D and SEQ ID NO:2 having been determined by sequencing a product of a polymerase chain reaction (PCR) mixture using DNA from a human cDNA library in a phage vector for the template, primed by vector-specific primers 5' and 3' to the cDNA insert site. As one of ordinary skill would appreciate, due to the possibilities of sequencing errors discussed above, the actual FGF-13 polypeptide encoded by the deposited cDNA, which comprises about 212 amino acids at the C-terminal end of the sequence in SEQ ID NO:2, may be somewhat longer or shorter than the determined sequence. More generally, the actual open reading frame may be anywhere in the range of ±20 amino acids, more likely in the range of ±10 amino acids, of that predicted from the N-terminus shown in FIGS. 1A–D (SEQ ID NO:1).

Leader and Mature Sequences

The amino acid sequence of the complete FGF-13 protein includes a leader sequence and a mature protein, as shown in SEQ ID NO:2. More in particular, the present invention provides nucleic acid molecules encoding a mature form of the FGF-13 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature FGF-13 polypeptide having the amino acid sequence encoded by the cDNA clone contained in the host identified as ATCC Deposit No. 97148. By the "mature FGF-13 polypeptide having the amino acid sequence encoded by the cDNA clone in ATCC Deposit No. 97148" is meant the mature form(s) of the FGF-13 protein produced by expression in a mammalian cell (e.g., COS cells, as described below) by a DNA encoding the complete FGF-13 coding sequence encoded by the human DNA sequence of the clone contained in the vector in the deposited host, when that human DNA sequence is operably linked to appropriate regulatory sequences for translation of the FGF-13 coding sequence including an initiation codon.

In the present case, the deduced amino acid sequence of the complete FGF-13 polypeptide was analyzed by alignment with the known amino acid sequence of human FGF-8 (see FIG. 2), thereby predicting a secretory leader cleavage site at the homologous location within the complete amino acid sequence shown in SEQ ID NO:2, between residues −1 and +1.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with or without an initiation codon at positions 1 to 3 of the nucleotide sequence shown in FIGS. 1A–D (SEQ ID NO:1). Also included are DNA molecules comprising the coding sequence for the predicted mature FGF-13 protein shown at positions 1 to 193 of SEQ ID NO:2.

In addition, isolated nucleic acid molecules of the invention include DNA molecules which comprise a sequence substantially different from those described above but which, due to the degeneracy of the genetic code, still encode an FGF-13 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the FGF-13 polypeptide having an amino acid sequence encoded by the cDNA clone contained in the plasmid deposited as ATCC Deposit No. 97148 on May 12, 1995. Preferably, this nucleic acid molecule will encode the mature polypeptide encoded by the above-described deposited cDNA clone.

The invention further provides an isolated nucleic acid molecule having the nucleotide sequence shown in FIGS. 1A–D (SEQ ID NO:1) or the nucleotide sequence of the FGF-13 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the FGF-13 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1 to 648 of SEQ ID NO:1.

Thus, the invention includes a polynucleotide comprising any portion of at least about 30 nucleotides, preferably at least about 50 nucleotides, of SEQ ID NO:1 from residue 1 to 648. More generally, by a fragment of an isolated nucleic acid molecule having the nucleotide sequence of the deposited cDNA or the nucleotide sequence shown in FIGS. 1A–D (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A–D (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A–D (SEQ ID NO:1). Preferred nucleic acid fragments of the present invention include nucleic acid molecules encoding epitope-bearing portions of the FGF-13 polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97148. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 $\mu$g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–D (SEQ ID NO:1)). Of course, a polynucleotide which hybridizes only to a poly A sequence (such as the 3' terminal poly(A) tract of the FGF-13 cDNA shown in FIGS. 1A–D (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an FGF-13 polypeptide may include, but are not limited to those encoding the amino acid sequence of the mature polypeptide, by itself; and the coding sequence for the mature polypeptide and additional sequences, such as those encoding the about 25 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the FGF-13 fused to Fc at the N- or C-terminus.

Variant and Mutant Polynucleotides

The present invention further relates to variants of the nucleic acid molecules of the present invention, which encode portions, analogs or derivatives of the FGF-13 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the FGF-13 protein or portions thereof. Also especially preferred in this regard are conservative substitutions.

Most highly preferred are nucleic acid molecules encoding the mature protein having the amino acid sequence shown in SEQ ID NO:2 or the mature FGF-13 amino acid sequence encoded by the deposited cDNA clone.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the FGF-13 polypeptide having the complete amino acid sequence in SEQ ID NO:2; (b) a nucleotide sequence encoding the predicted mature FGF-13 polypeptide having the amino acid sequence at positions 1 to 193 of SEQUENCE ID NO:2; (c) a nucleotide sequence encoding the FGF-13 polypeptide having the complete amino acid sequence encoded by the cDNA clone contained in ATCC Deposit No. 97148; (d) a nucleotide sequence encoding the mature FGF-13 polypeptide having the amino acid sequence encoded by the cDNA clone contained in ATCC Deposit No. 97148; and (e) a nucleotide sequence complementary to any of the nucleotide sequences in (a), (b), (c) or (d) above.

By a polynucleotide having a nucleotide sequence at least, for example, 95% "identical" to a reference nucleotide sequence encoding an FGF-13 polypeptide is intended that the nucleotide sequence of the polynucleotide is identical to the reference sequence except that the polynucleotide sequence may include up to five point mutations per each 100 nucleotides of the reference nucleotide sequence encoding the FGF-13 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having FGF-13 activity. This is because even where a particular nucleic acid molecule does not encode a polypeptide having FGF-13 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having FGF-13 activity include, inter alia, (1) isolating the FGF-13 gene or allelic variants thereof in a cDNA library; (2) in situ hybridization (e.g., "FISH") to metaphase chromosomal spreads to provide precise chromosomal location of the FGF-13 gene, as described in Verna et al., *Human Chromosomes: A Manual of Basic Techniques*, Pergamon Press, New York (1988); and Northern blot analysis for detecting FGF-13 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having FGF-13 protein activity. By "a polypeptide having FGF-13 activity" is intended polypeptides exhibiting activity similar, but not necessarily identical, to an activity of the mature FGF-13 protein of the invention, as measured in a particular biological assay. For example, the FGF-13 protein of the present invention stimulates proliferations of various mammalian cells, particularly fibroblasts, as described further below.

FGF-13 protein stimulates cellular proliferation in a dose-dependent manner in the various activity assays described hereinbelow. Thus, "a polypeptide having FGF-13 protein activity" includes polypeptides that also exhibit any of the same activities in the below-described assays in a dose-dependent manner. Although the degree of dose-dependent activity need not be identical to that of the FGF-13 protein, preferably, "a polypeptide having FGF-13 protein activity" will exhibit substantially similar dose-dependence in a given activity as compared to the FGF-13 protein (i.e., the candidate polypeptide will exhibit greater activity or not more than about 25-fold less and, preferably, not more than about tenfold less activity relative to the reference FGF-13 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having FGF-13 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having FGF-13 protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of FGF-13 polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH6a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al, *J. Biol. Chem.* 270:9459–9471 (1995).

The FGF-13 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated FGF-13 polypeptide comprising the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of FGF-13 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, polypeptides having deletions of up to about 10 additional N-terminal residues beyond the predicted leader cleavage point (i.e., up to the Asparagine at position 10 in SEQ ID NO:2) can retain some biological activity such as cell proliferation stimulating or receptor binding activity.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature from of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the FGF-13 shown in SEQ ID NO:2, up to the Asparagine at position 10. In particular, the present invention provides polypeptides comprising the amino acid sequence of residues n-193 of SEQ ID NO:2, where n is an integer other than zero in the range of −23 to +10 (excepting zero). More in particular, the invention provides polynucleotides encoding polypeptides having the amino acid sequence of residues of −23 to 193, −22 to 193, −21 to 193, −20 to 193, −19 to 193, −18 to 193, −17 to 193, −16 to 193, −15 to 193, −14 to 193, −13 to 193, −12 to 193, −11 to 193, −10 to 193, 31 9 to 193, −8 to 193, −7 to 193, −6 to 193, −5 to 193, −4 to 193, −3 to 193, −2 to 193, −1 to 193, 1 to 193, 2 to 193, 3 to 193, 4 to 193, 5 to 193, 6 to 193, 7 to 193, 8 to 193, 9 to 193, and 10 to 193 of SEQ ID NO:2. Polynucleotides encoding these polypeptides also are provided.

Similarly, many examples of biologically functional C-terminal deletion muteins are known. For instance, interferon gamna shows up to ten times higher activities by deleting 8–10 amino acid residues from the carboxy terminus of the protein (Döbeli et al., *J. Biotechnology* 7:199–216 (1988). In the present case, since the protein of the invention is homolgous to human FGF-8, deletions of C-terminal amino acids up to the conserved region beginning with the Leucine at position 154 in SEQ ID NO:2 can retain some biological activity such as stimulation of cellular proliferation or receptor binding.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the FGF-3 shown in SEQ ID NO:2, up to the Leucine at position 154 of SEQ ID NO:2, and polynucleotides encoding such polypeptides. In particular, the present invention provides polypeptides having the amino acid sequence of residues −22 to m of the amino acid sequence in SEQ ID NO:2, where m is any integer in the range of 154 to 192, and residue 154 is the position of the first residue from the C-terminus of the complete FGF-13 polypeptide (shown in SEQ ID NO:2) which begins the region highly conserved between FGF-13 and human FGF-8.

More in particular, the invention provides polynucleotides encoding polypeptides having the amino acid sequence of residues −22 to 154, −22 to 155, −22 to 156, −22 to 157, −22 to 158, −22 to 159, −22 to 160, −22 to 161, −22 to 162, −22 to 163, −22 to 164, −22 to 165, −22 to 166, −22 to 167, −22 to 168, −22 to 169, −22 to 170, −22 to 171, −22 to 172, −22 to 173, −22 to 174, −22 to 175, −22 to 176, −22 to 177, −22 to 178, −22 to 179, −22 to 180, −22 to 181, −22 to 182, −22 to 183, −22 to 184, −2 to 185, −22 to 186, −22 to 187, −22 to 188, −22 to 189, −22 to 190, and −22 to 192 of SEQ ID NO:2. Polynucleotides encoding these polypeptides also are provided.

The invention also provides polypeptides having one or more amino acids deleted from both the amino and the carboxyl termini, which may be described generally as having residues n–m of SEQ ID NO:2, where n and m are integers as described above.

Also included are a nucleotide sequence encoding a polypeptide consisting of a portion of the complete FGF-13 amino acid sequence encoded by the cDNA clone contained in ATCC Deposit No. 97148, where this portion excludes from 1 to about 33 amino acids from the amino terminus of the complete amino acid sequence encoded by the cDNA clone contained in ATCC Deposit No. 97148, or from 1 to about 39 amino acids from the carboxy terminus, or any combination of the above amino terminal and carboxy terminal deletions, of the complete amino acid sequence encoded by the cDNA clone contained in ATCC Deposit No. 97148. Polynucleotides encoding all of the above deletion mutant polypeptide forms also are provided.

Other Mutants

In addition to terminal deletion forms of the protein discussed above, it also will be recognized by one of ordinary skill in the art that some amino acid sequences of the FGF-13 polypeptide can be varied without significant effect of the structure or function of the protein. If such differences in sequence are contemplated, it should be remembered that there will be critical areas on the protein which determine activity.

Thus, the invention further includes variations of the FGF-13 polypeptide which show substantial FGF-13 polypeptide activity or which include regions of FGF-13 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the FGF-13 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |

TABLE 1-continued

Conservative Amino Acid Substitutions.

| | |
|---|---|
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the FGF-13 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the FGF-13 polypeptide can be substantially purified by the one-step method described in Smith and Johnson, *Gene* 67:31–40 (1988). Polypeptides of the invention also can be purified from natural or recombinant sources using anti-FGF-13 antibodies of the invention in methods which are well known in the art of protein purification.

The invention further provides an isolated FGF-13 polypeptide comprising an amino acid sequence selected from the group consisting of: (a) the amino acid sequence of the complete FGF-13 polypeptide shown in SEQ ID NO:2 excepting the N-terminal methionine (i.e., positions −22 to 193 of SEQ ID NO:2); (b) the amino acid sequence of the predicted mature FGF-13 polypeptide from about position 1 to about position 193 in SEQ ID NO:2; (c) the amino acid sequence of the FGF-13 polypeptide having the complete amino acid sequence encoded by the cDNA clone contained in ATCC Deposit No. 97148; and (d) the amino acid sequence of the mature FGF-13 polypeptide having the amino acid sequence encoded by the cDNA clone contained in ATCC Deposit No. 97148.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of an FGF-13 polypeptide is intended that the amino acid sequence of the polypeptide is identical to the reference sequence except that the polypeptide sequence may include up to five amino acid alterations per each 100 amino acids of the reference amino acid of the FGF-13 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence: These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting FGF-13 protein expression as described below or as agonists and antagonists capable of enhancing or inhibiting FGF-13 protein function. Further, such polypeptides can be used in the yeast two-hybrid system to "capture" FGF-13 protein binding proteins which are also candidate agonists and antagonists according to the present invention. The yeast two hybrid system is described in Fields and Song, *Nature* 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science*, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate FGF-13-specific antibodies include: a polypeptide comprising amino acid residues in SEQ ID NO:2 from about Gin 22 to about Asn 32, about Asn 34 to about Met 43, about Gln 46 to about Tyr 55, about Ser 59 to about Val 66, about Val 68 to about Phe 83, about Val 88 to about Glu 105, about Met 110 to about Val 128, about Phe 153 to about His 173, about Leu 178 to about Gln 182, about Phe 185 to about Gln 194, and about Val 198 to about Gln 213. These polypeptide fragments have been determined to bear antigenic epitopes of the FGF-13 protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al, *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, FGF-13 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86 (1988)). Fusion proteins that have a disulfide-linked dimeric structure due to the IgG part can also be more efficient in binding and neutralizing other molecules than the monomeric FGF-13 protein or protein fragment alone (Fountoulakis et al., *J. Biochem.* 270:3958–3964 (1995)).

Antibodies

FGF-13-protein specific antibodies for use in the present invention can be raised against the intact FGF-13 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to FGF-13 protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the FGF-13 protein or an antigenic fragment thereof can be administered to an animal in order to induce the production of sera containing polyclonal antibodies. In a preferred method, a preparation of FGF-13 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or FGF-13 protein binding fragments thereof). Such monoclonal antibodies can be prepared using hybridoma technology (Köhler et al., *Nature* 256:495 (1975); Köhler et al., *Eur. J Immunol.* 6:511 (1976); Köhler et al., Eur. J. Immunol. 6:292 (1976); Hammerling et al., in: *Monoclonal Antibodies and T-Cell Hybridomas*, Elsevier, N.Y., (1981) pp. 563–681 ). In general, such procedures involve immunizing an animal (preferably a mouse) with an FGF-13 protein antigen or, more preferably, with an FGF-13 protein-expressing cell. Suitable cells can be recognized by their capacity to bind anti-FGF-13 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Manassas, Va. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the FGF-13 protein antigen.

Alternatively, additional antibodies capable of binding to the FGF-13 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, FGF-13-protein specific antibodies are used to immunize an animal, preferably a mouse. The splenocytes of such an animal are then used to produce hybridoma cells, and the hybridoma cells are screened to identify clones which produce an antibody whose ability to bind to the FGF-13 protein-specific antibody can be blocked by the FGF-13 protein antigen. Such antibodies comprise anti-idiotypic antibodies to the FGF-13 protein-specific antibody and can be used to immunize an animal to induce formation of further FGF-13 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, FGF-13 protein-binding fragments can be produced through the application of recombinant DNA technology or through synthetic chemistry.

For in vivo use of anti-FGF-13 in humans, it may be preferable to use "humanized" chimeric monoclonal antibodies. Such antibodies can be produced using genetic constructs derived from hybridoma cells producing the monoclonal antibodies described above Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et a., *Nature* 314:268 (1985).

FGF-13-Related Disorders
Diagnosis

This invention is also related to the use of the genes of the present invention as part of a diagnostic assay for detecting diseases or susceptibility to diseases related to the presence of mutations in the nucleic acid sequences encoding the polypeptide of the present invention.

Individuals carrying mutations in a gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324: 163–166 (1986)) prior to analysis. RNA or cDNA may also be used for the same purpose. As an example, PCR primers complementary to the nucleic acid encoding a polypeptide of the present invention can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of FGF-13 proteins in various tissues since an over-expression of the proteins compared to normal control tissue samples may detect the presence of abnormal cellular proliferation, for example, a tumor. Assays used to detect levels of protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to an antigen to the polypeptides of the present invention, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme.

A sample is removed from a host and incubated on a solid support, e.g. a polystyrene dish, that binds the proteins in the sample. Any free protein binding sites on the dish are then covered by incubating with a non-specific protein like bovine serum albumen. Next, the monoclonal antibody is incubated in the dish during which time the monoclonal antibodies attach to any polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the protein of interest.

Unattached reporter antibody is then washed out. Peroxidase substrates are then added to the dish and the amount of color developed in a given time period is a measurement of the amount of a polypeptide of the present invention present in a given volume of patient sample when compared against a standard curve.

A competition assay may be employed wherein antibodies specific to a polypeptide of the present invention are attached to a solid support and labeled FGF-13 and a sample derived from the host are passed over the solid support and the amount of label detected, for example by liquid scintillation chromatography, can be correlated to a quantity of a polypeptide of the present invention in the sample. is A "sandwich" assay is similar to an ELISA assay. In a "sandwich" assay a polypeptide of the present invention is passed over a solid support and binds to antibody attached to a solid support. A second antibody is then bound to the polypeptide of interest. A third antibody which is labeled and specific to the second antibody is then passed over the solid support and binds to the second antibody and an amount can then be quantified.

The present inventors have discovered that FGF-13 is expressed in cancerous ovarian tissue as well as fetal kidney and fetal brain tissue. Thus, cancers of these tissues as well as other cancerous tissues in mammals can express significantly enhanced levels of the FGF-13 protein and mRNA encoding the FGF-13 protein when compared to a corresponding "standard" level. Further, it is believed that enhanced levels of the FGF-13 protein can be detected in certain body fluids (e.g., sera, plasma, urine, and spinal fluid) from mammals with such a cancer when compared to sera from mammals of the same species not having the cancer. Thus, the invention provides a diagnostic method useful during diagnosis of a disorder involving FGF-13 expression, including cancers, which involves measuring the expression level of the gene encoding the FGF-13 protein in ovarian, renal or neurological system tissue or other cells or body fluid from an individual and comparing the measured gene expression level with a standard FGF-13 gene expression level in that tissue, cell or fluid, whereby an increase or decrease in the gene expression level compared to the standard is indicative of a disorder related to FGF-13 expression.

Where a diagnosis of a disorder in the ovarian, renal or neurological system, including diagnosis of a tumor, has already been made according to conventional methods, the present invention is useful as a prognostic indicator, whereby patients exhibiting enhanced or reduced FGF-13 gene expression will experience a worse clinical outcome relative to patients expressing the gene at a level nearer the standard level.

By "assaying the expression level of the gene encoding the FGF-13 protein" is intended qualitatively or quantitatively measuring or estimating the level of the FGF-13 protein or the level of the mRNA encoding the FGF-13 protein in a first biological sample either directly (e.g., by determining or estimating absolute protein level or mRNA level) or relatively (e.g., by comparing to the FGF-13 protein level or mRNA level in a second biological sample). Preferably, the FGF-13 protein level or mRNA level in the first biological sample is measured or estimated and compared to a standard FGF-13 protein level or mRNA level, the standard being taken from a second biological sample obtained from an individual not having the disorder or being determined by averaging levels from a population of individuals not having a disorder related to FGF-13 expression. As will be appreciated in the art, once a standard FGF-13 protein level or mRNA level is known, it can be used repeatedly as a standard for comparison.

By "biological sample" is intended any biological sample obtained from an individual, body fluid, cell line, tissue culture, or other source which contains FGF-13 protein or mRNA. As indicated, biological samples include body fluids (such as sera, plasma, urine, synovial fluid and spinal fluid) which contain free FGF-13 protein, ovarian or renal system tissue, and other tissue sources found to express complete or mature FGF-13 polypeptide or an FGF-13 receptor. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the FGF-13 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying FGF-13 protein levels in a biological sample can occur using antibody-based techniques. For example, FGF-13 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting FGF-13 protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying FGF-13 protein levels in a biological sample obtained from an individual, FGF-13 protein can also be detected in vivo by imaging. Antibody labels or markers for in vivo imaging of FGF-13 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A FGF-13 protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain FGF-13 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage associated with stroke and which occurs in certain neuronal disorders or neuro-degenerative conditions such as Alzheimer's disease, Parkinson's disease, and AIDS related complex. FGF-13 increases the number of dopaminergic neurons surviving invitro indicating that it may benefit the Parkinson's disease patient. FGF-13 has the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The FGF-13 polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The FGF-13 polypeptide may also be employed to maintain organs before transplantation or for supporting cell culture of primary tissues.

The polypeptide of the present invention may also be employed for inducing tissue of mesodermal origin to differentiate in early embryos.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

This invention provides a method for identification of the receptors for the polypeptides of the present invention. The genes encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Figure 13:
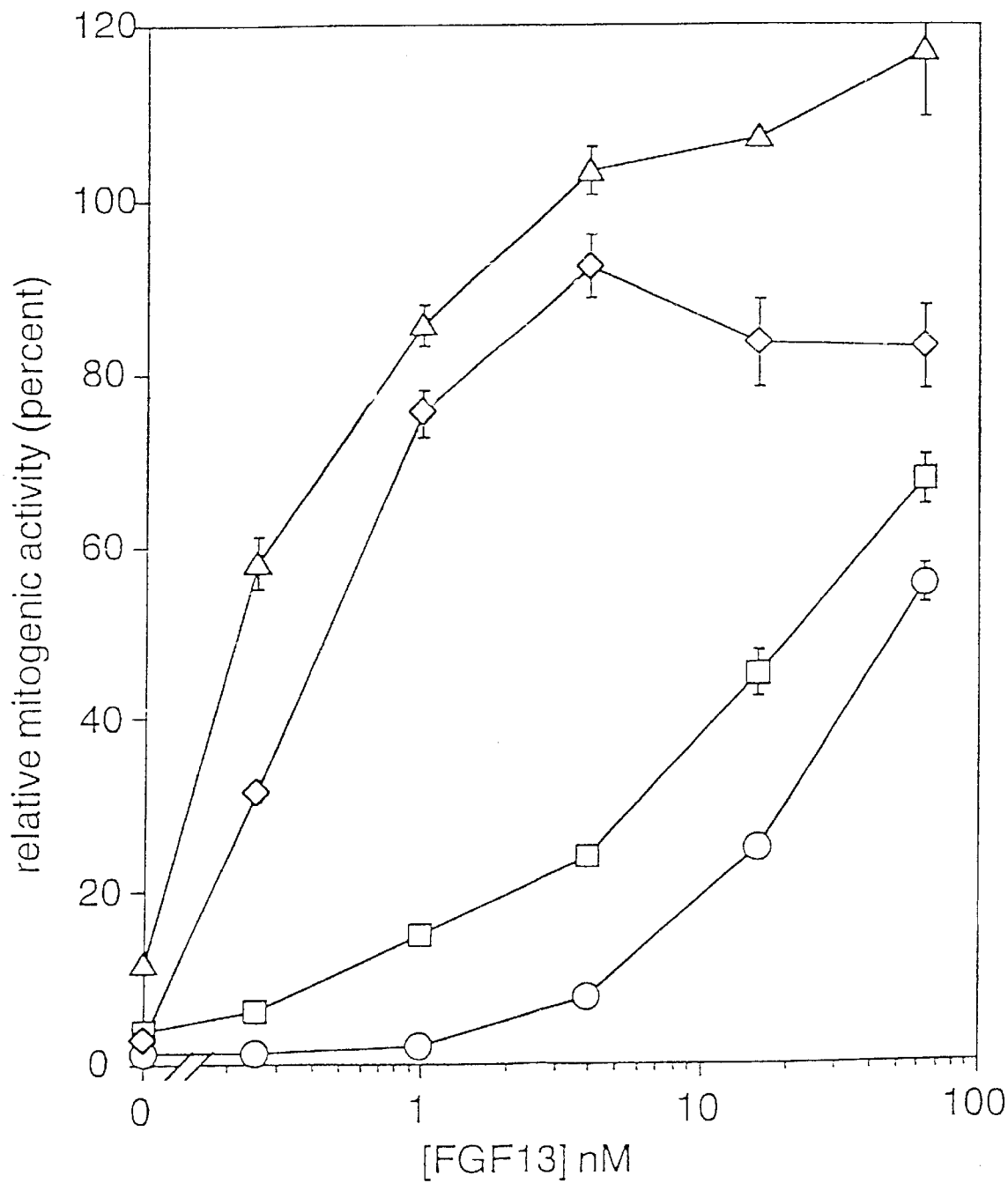
FIG. 13 shows mitogenic activity of FGF13 on BaF3 cells expressing FGF receptors (FGFR) 1c, 2c, 3c, and 4 measured by thymidine incorporation. BaF3 cells expressing FGF receptors were incubated with FGF-13 up to concentration of 62.5 nM (X axis). aFGF at the same concentration range was used as a positive control. The Y axis represents the amount of $^3$H thymidine incorporated into DNA of BaF3 cells as a percentage of the maximum cpm incorporated following FGF1 stimulation. Circle: FGFR1c; Square: FGFR2c; Diamond: FGFR3c; Triangle: FGFR4.

As a further approach to identifying the specific class(es) of known FGF-specific receptors which bind FGF-13, recombinant human FGF-13 protein was assayed for mitogenic activity on BaF3 cell lines engineered to express individual FGF receptors (Ornitz et al., *J. Biol. Chem.,* 271:15292–15297 (1996)). These experiments demonstrate that FGF-13 preferentially activates FGF receptors 3c and 4 and has some activity toward FGF receptors 1c and 2c. See FIG. 13. No activity was detected toward the "b" splice variants of any FGF receptor. Overall, this is a similar receptor specificity pattern to that of FGF-8. However, the overall activity of recombinant FGF-13 is considerably lower than that of other FGFs, suggesting that the particular preparation of this recombinant protein which was tested was not fully active.

Formulations

The FGF-13 polypeptide composition will be formulated and dosed in a fashion consistent with good medical practice, taking into account the clinical condition of the individual patient (especially the side effects of treatment with FGF-13 polypeptide alone), the site of delivery of the FGF-13 polypeptide composition, the method of administration, the scheduling of administration, and other factors known to practitioners. The "effective amount" of FGF-13 polypeptide for purposes herein is thus determined by such considerations.

The polypeptides, agonists and antagonists of the present invention may be employed in combination with a suitable pharmaceutical carrier to comprise a pharmaceutical composition for parenteral administration. Such compositions comprise a therapeutically effective amount of the polypeptide, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc. In the specific case of topical administration, dosages are preferably administered from about 0.1 µg to 9 mg per $cm^2$.

The polypeptide of the invention and agonist and antagonist compounds which are polypeptides, may also be employed in accordance with the present invention by expression of such polypeptide in vivo, which is often referred to as "gene therapy."

Thus, for example, cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, .Myeloproliferative Sarcoma Virus, and mammary tumor virus. In one embodiment, the retroviral plasmid vector is derived from Moloney Murine Leukemia Virus.

The vector includes one or-more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, -2, -AM, PA12, T19-14X, VT-19-17-H2, CRE, CRIP, GP+E-86, GP+envAm12, and DAN cell lines as described in Miller, Human Gene Therapy, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Agonists and Antagonists—Assays and Molecules

This invention provides a method of screening compounds to identify those which modulate the action of the polypeptide of the present invention. An example of such an assay comprises combining a mammalian fibroblast cell, a the polypeptide of the present invention, the compound to be screened and $^3[H]$ thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3[H]$ thymidine in each case. The amount of fibroblast cell proliferation is measured by liquid scintillation chromatography which measures the incorporation of $^3[H]$ thymidine. Both agonist and antagonist compounds may be identified by this procedure.

In another method, a mammalian cell or membrane preparation expressing a receptor for a polypeptide of the present invention (as described above and in (Ornitz et al., supra) is incubated with a labeled polypeptide of the present invention in the presence of the compound. The ability of the compound to enhance or block this interaction could then be measured. Alternatively, the response of a known second messenger system following interaction of a compound to be screened and the FGF-13 receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

Examples of antagonist compounds include antibodies, or in some cases, oligonucleotides, which bind to the receptor for the polypeptide of the present invention but elicit no second messenger response or bind to the FGF-13 polypeptide itself. Alternatively, a potential antagonist may be a mutant form of the polypeptide which binds to the receptors, however, no second messenger response is elicited and, therefore, the action of the polypeptide is effectively blocked.

Another antagonist compound to the FGF-13 gene and gene product is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptides of the present invention. The antisense RNA oligonucleotide hybridizes to the mRNA in vivo and blocks translation of the mRNA molecule into the polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide.

Potential antagonist compounds also include small molecules which bind to and occupy the binding site of the receptors thereby making the receptor inaccessible to its polypeptide such that normal biological activity is prevented. Examples of small molecules include, but are not limited to, small peptides or peptide-like molecules.

Antagonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonists may also be employed to prevent hypervascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonists may also be employed to prevent the growth of scar tissue during wound healing.

Chromosome Assays

In certain preferred embodiments relating to chromosomal mapping, the cDNA herein disclosed-is used to clone genomic DNA of an FGF-13 gene. This can be accomplished using a variety of well known techniques and libraries, which generally are available commercially. The genomic DNA then is used for in situ chromosome mapping using well known techniques for this purpose. Therefore, the nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Using methods described above, the FGF-13 gene of the invention has been mapped by florescent in situ hybridization to human chromosome 8p21. The corresponding map position in the mouse includes several disease loci including ds (disorganization—developmental disruption) and wc (waved coat—homozygous lethality).

Having generally described the invention, the same will be more readily understood by reference to the following examples, which are provided by way of illustration and are not intended as limiting.

EXAMPLES

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p. preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described by the method of Graham, F. and Van der Eb, A., Virology, 52:456–457 (1973).

Example 1(a)

Expression and Purification of "His-tagged" FGF-13 in E. coli

The DNA sequence encoding FGF-13 ATCC # 97148, was initially amplified using PCR oligonucleotide primers corresponding to the 5' sequences of the polypeptide having the amino acid sequence from position 2 to position 193 of SEQ ID NO:2 and to the vector sequences 3' to the gene. Additional nucleotides corresponding to the gene were added to the 5' and 3' sequences respectively. The 5' oligonucleotide primer 5' GCCAGACCATGGAGAATCAC-CCGTCTCCTAAT 3' (SEQ ID NO:11) contains a Nco restriction enzyme site. The 3' sequence 5' GATTTAA-GATCTCGTGAGGGGCTGGGGCCG 3' (SEQ ID NO:12) contains complementary sequences to a BglII site and is followed by 18 nucleotides of FGF-13 coding sequence.

The restriction enzyme sites correspond to the restriction enzyme sites on the bacterial expression vector pQE-60 (Qiagen, Inc. Chatsworth, Calif. 91311). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 was then digested with NcoI and BglII. The amplified sequences were ligated into pQE-60 and were inserted in frame with the sequence encoding for the histidine tag and the ribosome binding site (RBS). The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized FGF-13 is purified from this solution by chromatography on a Nickel-Chelate column under conditions that allow for tight binding by proteins containing the 6-His tag (Hochuli, E. et al., J. Chromatography 411:177–184 (1984)). The proteins are eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the proteins are dialyzed to 10 mmolar sodium phosphate.

Example 1(b)

Expression and Purification of FGF-13 in E. coli

The bacterial expression vector pQE70 is used for bacterial expression in this example (QIAGEN, Inc., 9259 Eton Avenue, Chatsworth, Calif., 91311). pQE70 encodes ampicillin antibiotic resistance ("Amp") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the FGF-13 protein comprising the predicted mature form of the FGF-13 amino acid sequence (i.e., amino acids 1–193 of SEQ ID NO:2) was amplified from the deposited cDNA clone using PCR oligonucleotide primers which anneal to the amino terminal sequences encoding the desired portion of the FGF-13 protein and to sequences in the deposited construct 3' to the cDNA coding sequence. Additional nucleotides containing restriction sites to facilitate cloning in the pQE70 vector were added to the 5' and 3' sequences, respectively.

For cloning mature form of the FGF-13 protein, the 5' primer had the sequence 5' CTAGTC GCATGCAGGGGGAGAATCACCCGTCT 3' (SEQ ID NO:13) containing the underlined SphI restriction site, which includes an initiation codon and following the initiation codon, 21 nucleotides of the amino terminal coding sequence of the mature FGF-13 sequence in SEQ ID NO:2. One of ordinary skill in the art would appreciate, of course, that the point in the protein coding sequence where the 5' primer begins may be varied to amplify a desired portion of the complete protein shorter or longer than the mature form. The 3' primer had the sequence 5' GCTTGA AAGCTTCTACGTGAGGGGCTGGGGCCG 3' (SEQ ID NO:14) containing the underlined HindIII restriction site followed by a stop codon and 18 nucleotides complementary to the 3' end of the coding sequence in the FGF-13 DNA sequence in SEQ ID NO:1.

The amplified FGF-13 DNA fragments and the vector pQE70 were digested with SphI and HindIII and the digested DNAs were then ligated together. Insertion of the FGF-13 DNA into the restricted pQE70 vector places the FGF-13 protein coding region including its associated stop codon downstream from the IPTG-inducible promoter and in-frame with the initiating AUG in the 5' primer. The associated stop codon prevents translation of the six histidine codons downstream of the insertion point.

The ligation mixture was transformed into competent E. coli cells using standard procedures such as those described in Sambrook et al., *Molecular Cloning: a Laboratory Manual*, 2nd Ed.; Cold Spring Harbor Laboratory Press, Cold Spring Harbor, N.Y. (1989). E. coli strain M15/rep4, containing multiple copies of the plasmid pREP4, which expresses the lac repressor and confers kanamycin resistance ("Kan$^r$"), was used in carrying out the illustrative example described herein. This strain, which is only one of many that are suitable for expressing FGF-13 protein, is available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with both ampicillin (100 μg/ml) and kanamycin (25 μg/ml). The O/N culture was used to inoculate a large culture, at a dilution of approximately 1:25 to 1:250. The cells are grown to an optical density at 600 nm ("OD$^{600}$") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently were incubated further for 3 to 4 hours and were then harvested by centrifugation.

To purify the FGF-13 polypeptide, the cells were lysed in a microfluidizer and then stirred for 3–4 hours at 4° C. in 2M and then 6M guanidine-HCl, 50 mM tris-HCl, pH 7.5, 2 mM EDTA. FGF-13 protein was present in both the 2M and 6M GuHCl extracts. The combined GuHCl extract was quickly diluted into a buffer containing 30 mM Tris pH7.5, 5 mM EDTA, 200 mM NaCl, 20 ug/ml Pefabloc SC, 2 ug/ml E-64 (Boeringer Mannhein). The refolded FGF-13 was purified through poros 50 HS (PerSeptive Biosystem) cation exchange column at pH7. The HS purified protein was applied to a set of poros HQ 50/poros CM 20 (PerSeptive Biosystem) anion/cation columns in a tandem chromatographic mode. FGF-13 was eluted from the CM column with 20 column volumes of 0.2 to 1.25M NaCl linear gradient in 24 mM NaCl, and purification was finished with a S200 sepharcryl HR (Pharmacia) size exclusion column.

The GuHCl extracted protein appeared to be the same size as the starting material on SDS-PAGE and was greater than 60% pure. However, after refolding the protein showed three bands which appeared to be about 2 kD smaller on SDS-PAGE, suggesting that proteolytic degradation may have occurred during refolding. Refolded FGF-13 captured by a strong cation exchange on the poros HS 50 column eluted at 80% purity with 1M NaCl. The protein resulting from the set of tandem columns, which was eluted from the CM column with 600 mM NaCl, showed at least three different bands on SDS-PAGE: two upper bands at about 22 kD and one lower band at about 19 kD. In an attempt to separate the upper and lower bands, the CM purified FGF-13 was put through a S200 sepharcryl HR size exclusion column. A fraction containing mainly the upper bands was isolated. The upper bands and the lower band were analyzed by N-terminus microsequencing.

The purified FGF-13 was slot blotted onto a ProBlott membrane (Applied Biosystems, Inc. (ABI) and stained with Ponceau S (0.2% in 3% acetic acid). The band of interest was then excised, placed in a "Blot Cartridge" and subjected to N-terminal amino acid sequence analysis using a model ABI-494 sequencer (Perkin-Elmer-Applied Biosystems, Inc.) and the Gas-phase Blot cycles. The results showed that the N-terminal sequence of the upper doublet bands was as predicted for the QE70 expression construct including the N-terminal Met (i.e., MQGEN . . . ) while the lower MW band had an N-terminal sequence 21 amino acids shorter (i.e., TDQLS). These terminal sequences represented, respectively, 40% and 50% of all N-termini in the original unfractionated preparation. Fibroblast proliferation assays showed that the upper and lower fractions exhibited comparable, and both fractions were more active than the His-tagged FGF-13 made using the vector of Example 1(a). These assays also showed that FGF-13 can be frozen at −80° C. and thawed later without losing its activity. The upper and lower FGF-13 fractions were then combined for all further biological activity tests described herein, producing a mixture consisting of three bands with nearly equal intensity on SDS-PAGE, greater than 95% purity and a low endotoxin level of 2 EU/mg.

Example 2

Cloning and Expression of FGF-13 Protein in a Baculovirus Expression System

The DNA sequence encoding the full length FGF-13 protein, ATCC # 97148,is amplified using PCR oligonucleotide primers corresponding to the 5' and 3' sequences of the gene:

The FGF-13 5' primer has the sequence 5' CTAGTG-GATCCCGA GAATCACCCGTCTCCT 3' (SEQ ID NO:15) and contains a BamHI restriction enzyme site (in bold) such that cloning at this site will put the baculovirus signal sequence in frame with 18 nucleotides of the FGF-13 gene downstream of the putative FGF-13 signal peptide cleavage site.

The 3' primer has the sequence 5' CGACTTCTA-GAACCT CGGGGATCTGGCTCC 3' (SEQ ID NO:16) and contains the cleavage site for the restriction endonuclease XbaI and 18 nucleotides complementary to the 3' non-translated sequence of the gene. The amplified sequences are isolated from a 1% agarose gel using a commercially available kit ("Geneclean," BIO 101 Inc., La Jolla, Calif.). The fragment is then digested with the respective endonucleases and purified again on a 1% agarose gel. This fragment is designated F2.

The vector pA2gp (modification of pVL941 vector, discussed below) is used for the expression of the proteins using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant virus the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1, pAc373, pVL941 and pAcIM1 (Luckow, V. A. and Summers, M. D., Virology, 170:31–39).

The plasmid is digested with the restriction enzymes and dephosphorylated using calf intestinal phosphatase. by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E.coli* DH5 cells are then transformed and bacteria identified that contained the plasmid (pBacFGF-13) using the respective restriction enzymes. The sequence of the cloned fragment are confirmed by DNA sequencing.

5 μg of the plasmid pBacFGF-13 are co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmids, in each case, are mixed in a sterile well of microtiter plates containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in 35 mm tissue culture plates with 1 ml Grace's medium without serum. The plates are rocked back and forth to mix the newly added solution. The plates are then incubated for 5 hours at 27%C. After 5 hours the transfection solution is removed from the plate and 1 ml of Grace's insect medium supplemented with 10% fetal calf serum is added. The plates are put back into an incubator and cultivation continued at 27%C for four days.

After four days the supernatant is collected and plaque assays performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus is added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4%C.

Sf9 cells are grown in Grace's medium supplemented with 10% heat-inactivated FBS. The cells are infected with the recombinant baculovirus V-FGF-13 at a multiplicity of infection (MOI) of 2. Six hours later the medium is removed and replaced with SF900 II medium minus methionine and cysteine (Life Technologies Inc., Gaithersburg). 42 hours later 5 μCi of 35S-methionine and 5 μCi 35S cysteine (Amersham) are added. The cells are further incubated for 16 hours before they are harvested by centrifugation and the labelled proteins visualized by SDS-PAGE and autoradiography.

Example 3

Cloning and Expression of FGF-13 in Mammalian Cells

Example 3(a)

Cloning and Expression in COS Cells

The expression of the predicted mature FGF-13 polypeptide uses a plasmid, FGF-13-HA derived from a vector pcDNA3/Amp (Invitrogen) containing: 1) SV40 origin of replication, 2) ampicillin resistance gene, 3) *E.coli* replication origin, 4) CMV promoter followed by a polylinker region, an SV40 intron and polyadenylation site. DNA fragments encoding the entire FGF-13 precursor and an HA tag fused in frame to the 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The PCR amplified DNA fragments and the vector, pcDNA3/Amp, are digested with the respective restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant FGF-13 COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the FGF-13-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with 35S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

Example 3(b)

Cloning and Expression in CHO Cells

The vector pC4 is used for the expression of FGF-13 polypeptide. Plasmid pC4 is a derivative of the plasmid pSV2-dhfr (ATCC Accession No. 37146). To produce a soluble, secreted form of the polypeptide, the predicted mature is fused to the secretory leader sequence of the human IL-6 gene. The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke; R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the FGF-13 polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and XbaI and then dephosphorylated using calf intestinal phosphates by procedures known in the art. The vector is then isolated from a 1% agarose gel.

The DNA sequence encoding the mature FGF-13 polypeptide is amplified using PCR oligonucleotide primers corresponding to the 5' and 3' sequences of the desired portion of the gene. The 5' primer containing the underlined BamHI site which overlaps with a Kozak sequence, an AUG start codon, a sequence encoding the secretory leader peptide from the human IL-6 gene, and 21 nucleotides of the 5' coding region of the mature FGF-13 polypeptide, has the following sequence: 5' CTAGCC<u>GGATCC</u>GCCACCAT GAACTCCTTCTCCACAAGCGCCTTCGGTCCAGT TGCCTTCTCCCTGGGGCTGCTCCTGGTGTTGCCT GCTGCCTTCCC TGCCCCAGTTGTGAGACCAGGGG GAGAATCACCCGTCT 3' (SEQ ID NO:17). The 3' primer, containing the underlined XbaI and 18 of nucleotides complementary to the 3' coding sequence immediately before the stop codon as shown in FIG. 1 (SEQ ID NO:1), has the following sequence: 5' GCTTGA<u>TCTAGA</u>CG TGAGGGGCTGGGGCCG 3' (SEQ ID NO:18).

The amplified fragment is digested with the endonucleases BamHI and XbaI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37%C for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB 101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 5

FGF-13 Biological Effects

Astrocyte and Neuronal Assays

Recombinant FGF-13, expressed in *Escherichia coli* and purified as described above, was tested for activity in promoting the survival, neuritic outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment.

Figure 4:
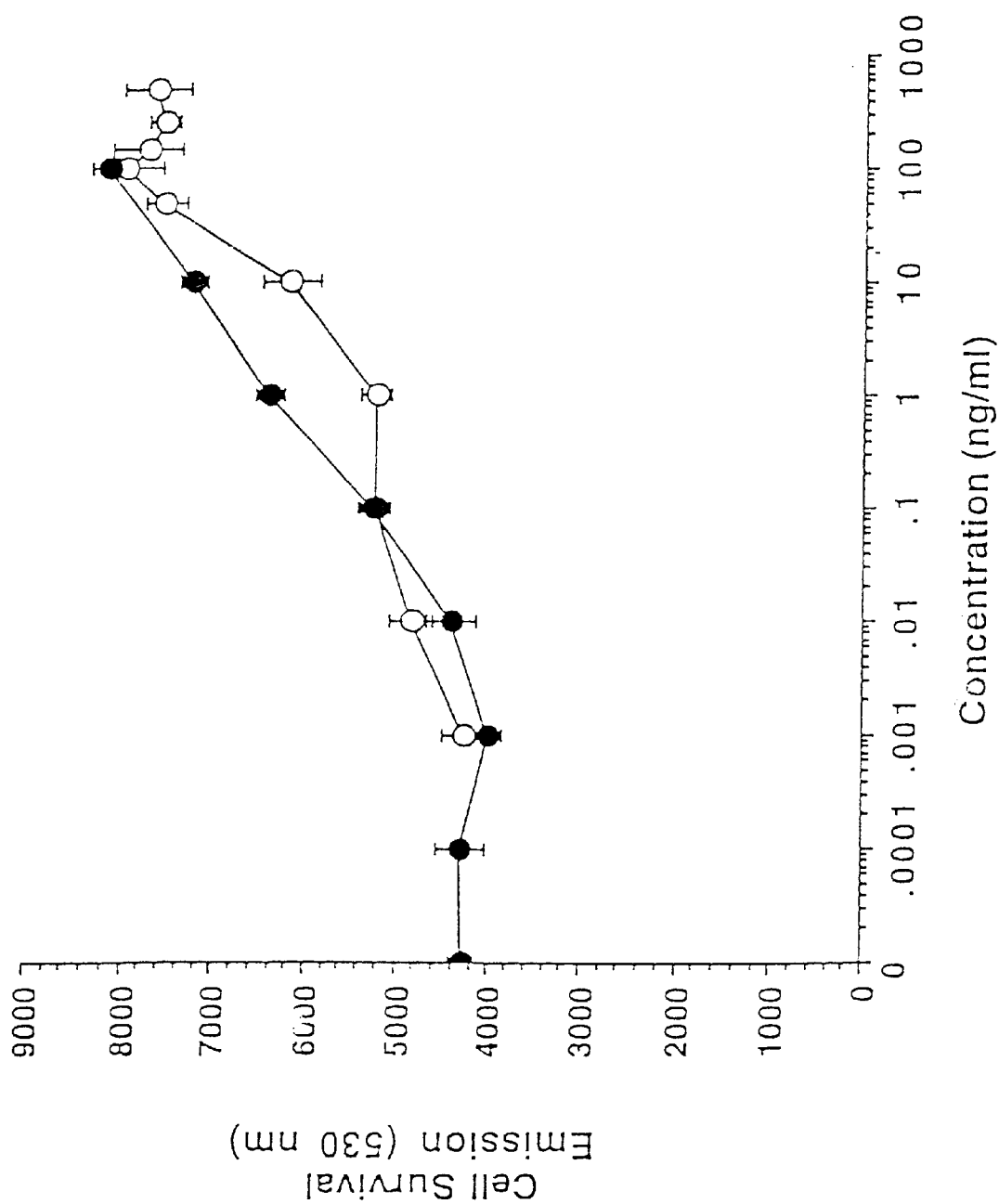
FIG. 4. FGF-13 treatment increases the number of cells in embryonic cortical cultures. The cells, derived from gestation day 17 embryos, were plated in polylysine/laminin coated wells at a density of 354 cells/mm$^2$. The cultures were maintained in serum-free medium and treated every other day with the indicated concentrations of FGFs. After treatment for 7–8 days, the cell number was estimated by labeling the cultures with Calcein AM and monitoring the level of fluorescence emission at 530 nm. The data points represent the mean of 5–6 determinations±the standard error. (Key: O=FGF-13; ●=bFGF(rh)).

Based on absorption measurements made with calcein AM, treatment with FGF-13 produced a dose dependent increase in the number of cells in cortical cultures (FIG. 4). Half-maximal and saturating responses to FGF-13 were observed at approximately 10 and 50 ng/ml, respectively, and were nearly equivalent, at saturation, to those observed with FGF-2, a previously characterized trophic factor for cortical neurons.

Figure 5:
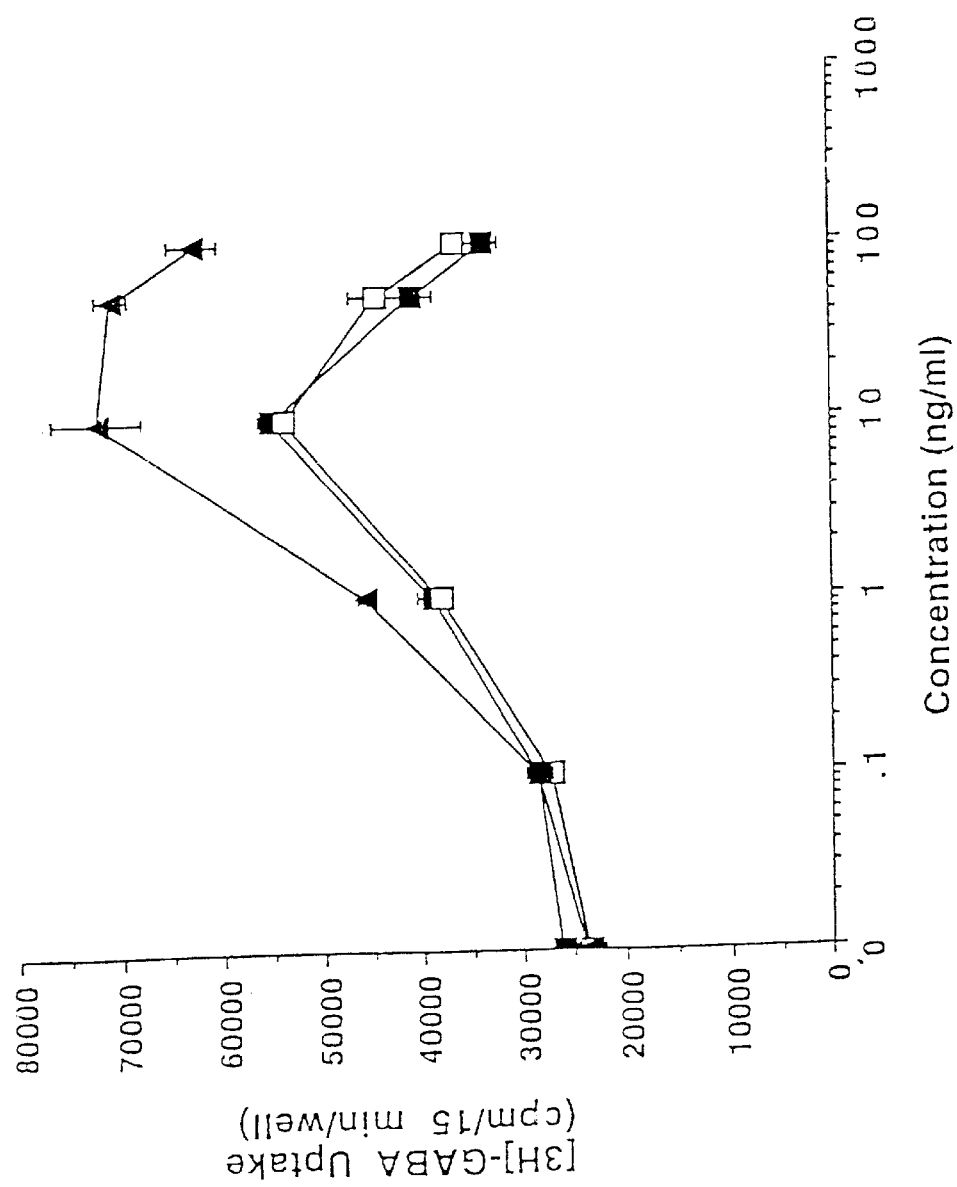
FIG. 5. The increase in high-affinity neuronal specific GABA-uptake induced by FGF-13 is enhanced by heparin. The cortical cultures, plated at a density of 1770 cells/mm2 in poly-lysine/laminin coated wells, were treated for 7–8 days with FGF-13 in the presence or absence of heparin. The heparin and FGF-13 were pre-incubated for approximately 30 min prior to addition to the cultures. The data points represent the means of 4 determinations±the standard error. (Key: ■=FGF-13; =FGF-13+10 ng/ml heparin; ▲=FGF-13+ 100 ng/ml heparin).

Since a change in calcein AM absorption does not discriminate between an increase in the glial or neuronal cell compartment, FGF-13 was tested to see whether it would induce a change in the level of phenotypic differentiation of one of the neuronal populations, the GABAergic neurons, present in the cortical cultures. After a 7 day treatment period, the level of high-affinity GABA-uptake increased as a function of the concentration of FGF-13 (FIG. 5). The GABAergic neuronal response appeared to be more sensitive to FGF-13 than the general cell survival response since the maximal induction of GABA-uptake occurred with 10 as opposed to 50 ng/ml of FGF-13.

Figure 6:
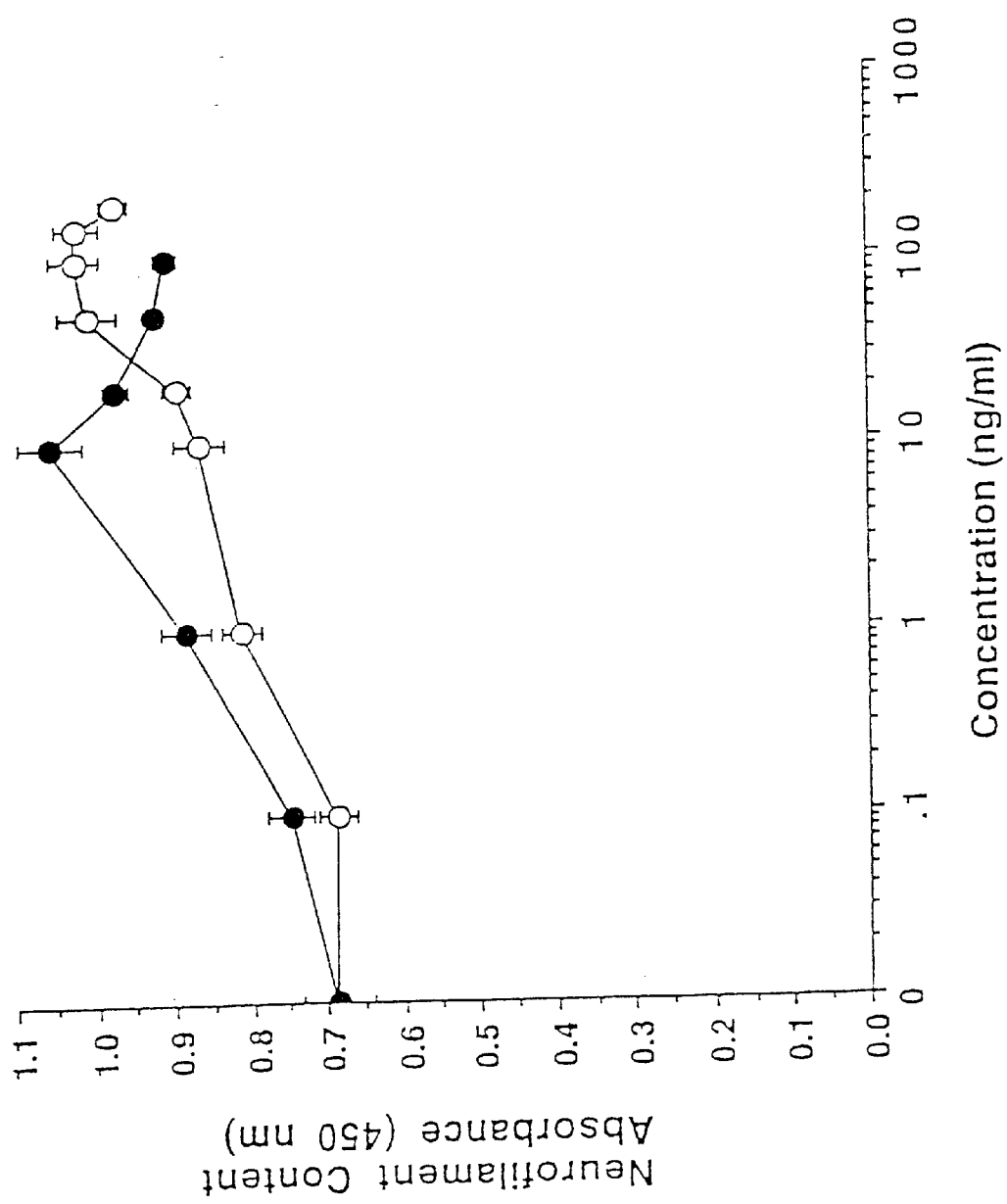
FIG. 6. FGF-13 treatment enhances neurite outgrowth of cortical neurons. For the neurite outgrowth experiments, the cultures were plated at a density of 212 cell/mm2 on poly-lysine coated wells. The cultures were then fixed and the amount of the 68 kDa neurofilament subunit was determined by ELISA. The data points are the means of 5–6 determinations±the standard error . . . (Key: O=FGF-13; ●=bFGF(rh)).

Previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." Proc. Natl. Acad. Sci. USA 83:3012–3016. (1986)). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of FGF-13 to induce neurite outgrowth was compared to the response achieved with FGF-2 (FIG. 6). Saturating responses to FGF-2 and FGF-13 were achieved with 10 and 50 ng/ml, respectively.

Figure 7:
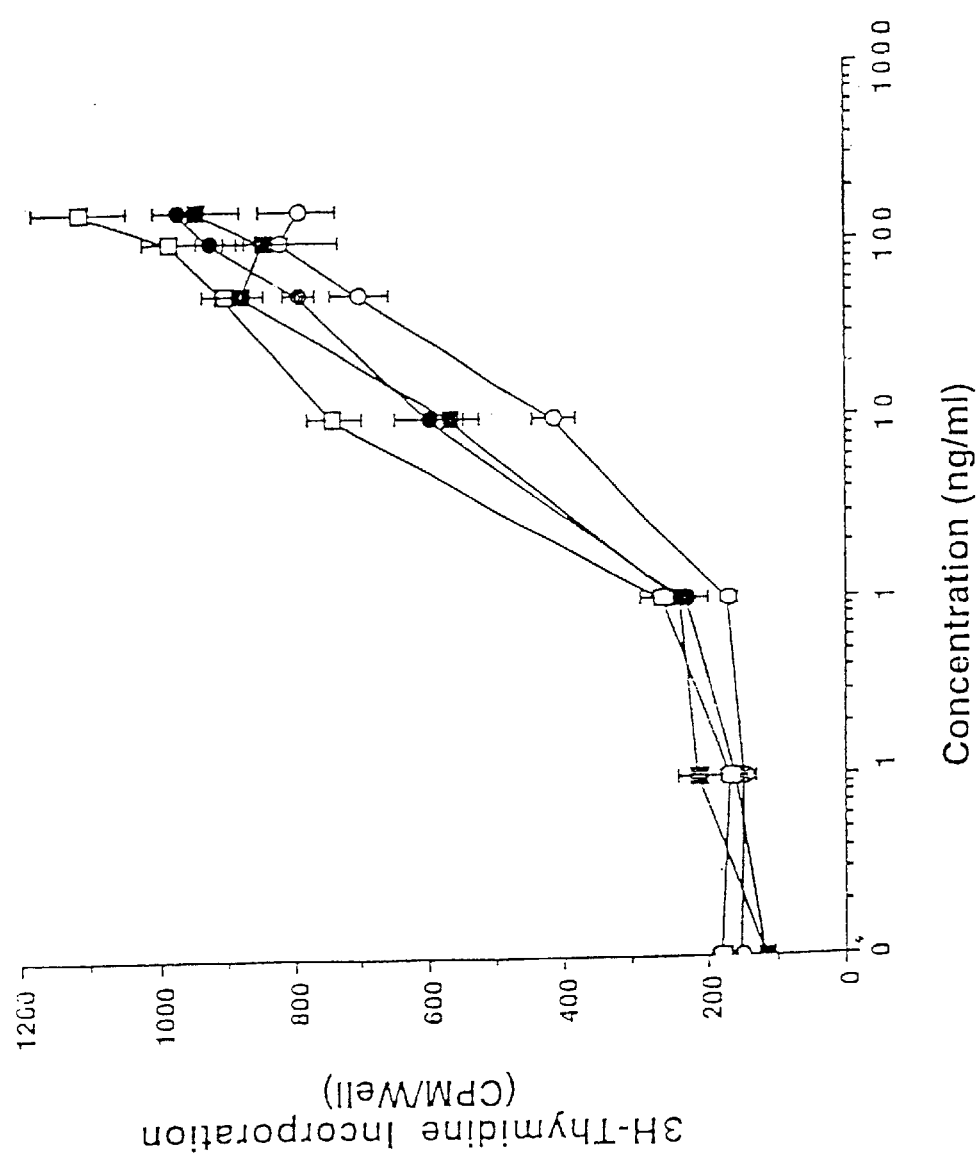
FIG. 7. FGF-13 induces the proliferation of rat hippocampal astrocytes. The astrocytes were sub-cultured at a density of 15,000 cells/well in 96 well plates. The cells were arrested in G1 phase by an 18 hr incubation in serum-free medium and then treated with FGF-13 in the absence or presence of heparin for 24 hours. During the last 4 hr of the incubation period, the cultures were labeled with [$^3$H]-thymidine. The data points represent the mean of 4–6 determinations±the standard error . . . (Key: O=FGF-13; ●=FGF-13+10 ng/ml heparin; =FGF-13+100 ng/ml heparin; ■=FGF-13+1000 ng/ml heparin).

Astrocytes are the major non-neuronal cell type present in the cortical cultures. FGF-1 (acidic FGF), FGF-2, and FGF-9 are mitogens for astrocytes. As shown in FIG. 7, FGF-1, FGF-2, or FGF-9 produced a 5- to 10-fold increase in the level of [$^3$H]-thymidine incorporation. In general, maximal responses were achieved in the range of 10 to 50 ng/ml. In comparison, treatment with FGF-13, in the presence of 100 ng/ml heparin, produced a concentration dependent increase in [$^3$H]-thymidine incorporation up to 150 ng/ml. The addition of heparin caused an apparent shift to the left in the dose response curve.

Figure 8:
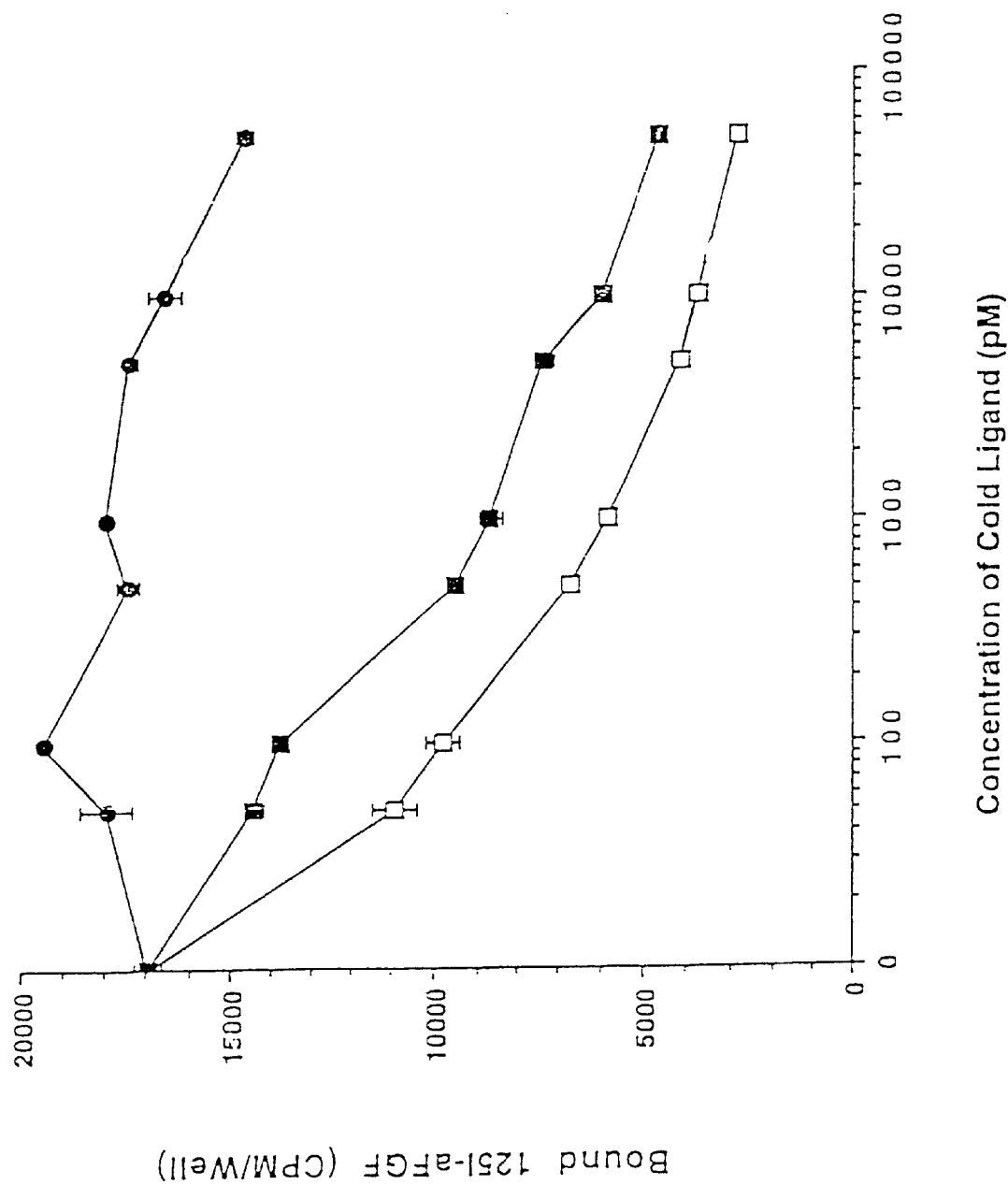
FIG. 8. FGF-13 displaces the binding of [$^{125}$I]FGF-1 from monolayer cultures of hippocampal astrocytes. Astrocytes were subcultured and grown to confluence in 24 well plates. The cultures were incubated at 4° C. with 50 pM [$^{125}$I] FGF-1 in the absence or presence of the indicated concentration of unlabeled FGFs. The data points are the means of 4 determinations±the standard error. (Key: ●=FGF-10; =bFGF; ■=FGF-13).

Heterologous ligand competition binding studies were conducted on membranes prepared from adult rat cortex. In these studies, the ability of FGF-13 to displace [$^{125}$I]-FGF-1 was monitored and compared to the displacement achieved with FGF-2. FIG. 8 summarizes the displacement curves for FGF-2, FGF-10, and FGF-13. The concentration of FGF-2 or FGF-13 required to achieve 50% displacement was 200 and 1000 pM, respectively.

Fibroblast and Endothelial Cell Assays

Human lung fibroblasts were obtained from Clonetics (San Diego, Calif.) and maintained in growth media from Clonetics. Dermal microvascular endothelial cells were obtained from Cell Applications (San Diego, Calif.). For proliferation assays, the human lung fibroblasts and dermal microvascular endothelial cells were cultured at 5,000 cells/well in a 96-well plate for one day in growth medium. The cells were then incubated for one day in 0.1% BSA basal medium. After replacing the medium with fresh 0.1% BSA medium, the cells were incubated with the test proteins for 3 days. Alamar Blue (Alamar Biosciences, Sacramento, Calif.) was added to each well to a final concentration of 10%. The cells were incubated for 4 hr. Cell viability was measured by reading in a CytoFluor fluorescence reader. For the $PGE_2$ assays, the human lung fibroblasts were cultured at 5,000 cells/well in a 96-well plate for one day. After a medium change to 0.1% BSA basal medium, the cells were incubated with FGF-2 or FGF-13 with or without IL-1α for 24 hours. The supernatants were collected and assayed for $PGE_2$ by EIA kit (Cayman, Ann Arbor, Mich.). For the IL-6 assays, the human lung fibroblasts were cultured at 5,000 cells/well in a 96-well plate for one day. After a medium change to 0.1% BSA basal medium, the cells were incubated with FGF-2 or FGF-13 with or without IL-1α for 24 hours. The supernatants were collected and assayed for IL-6 by ELISA kit (Endogen, Cambridge, Mass.).

Figure 9:
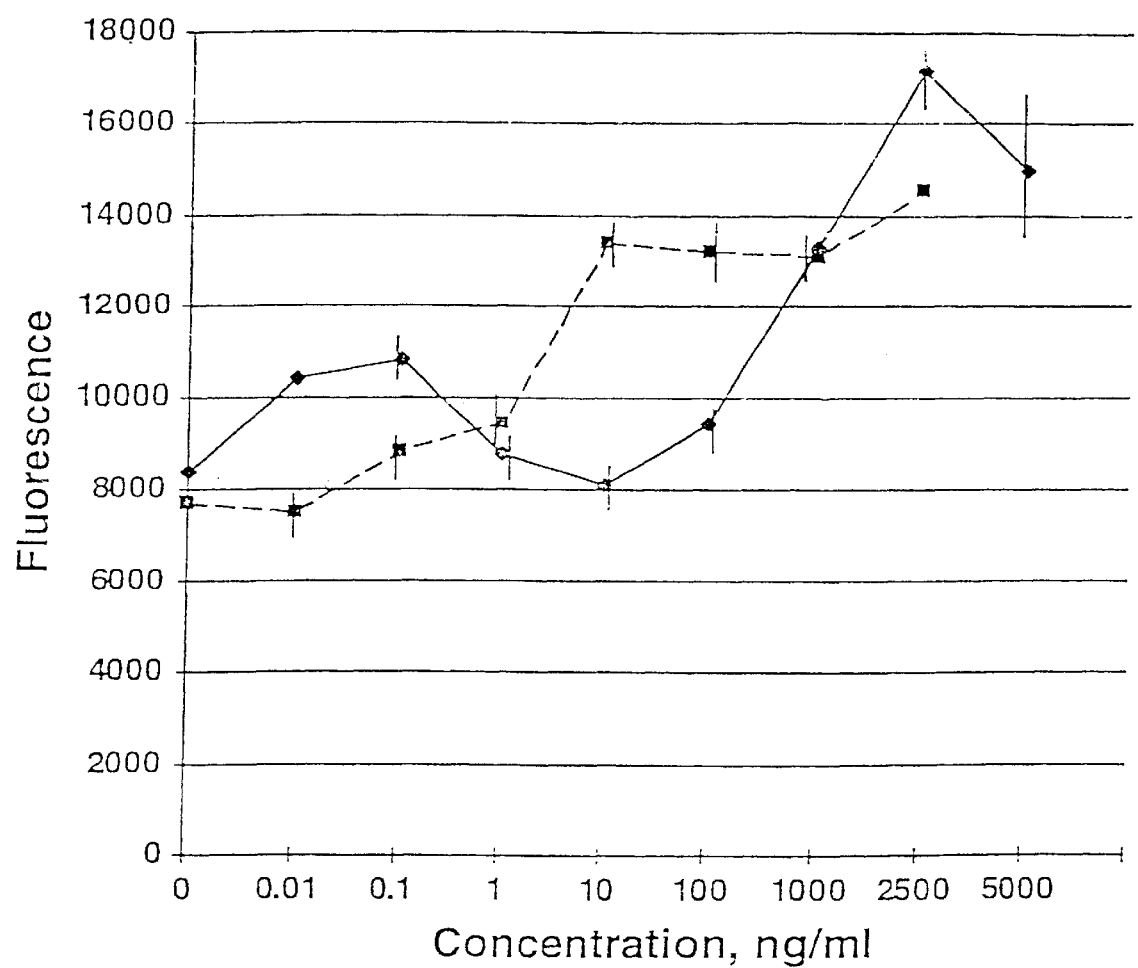
FIG. 9. Effect of FGF-13 treatment on human lung fibroblast proliferation. (Key: ■=bFGF; ♦=FGF-13).
Figure 10:
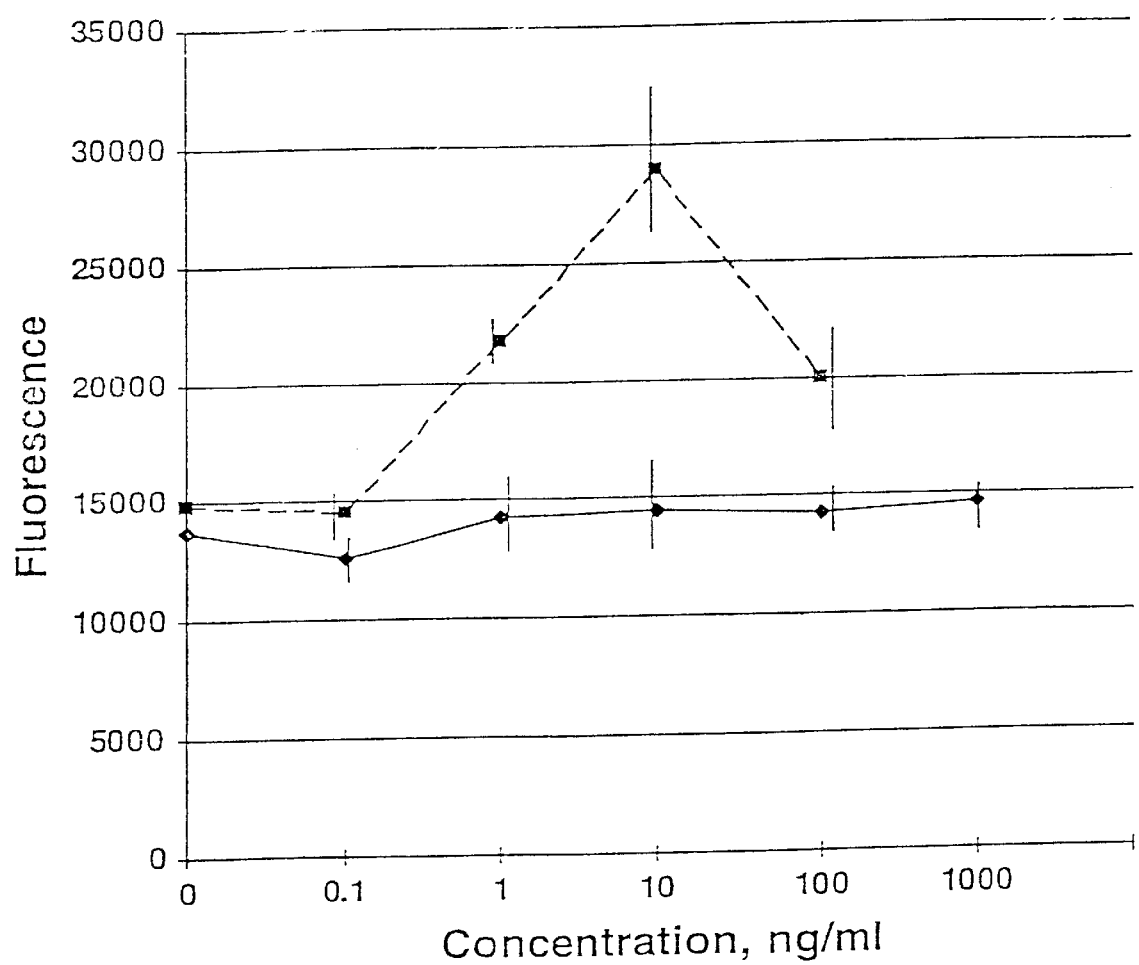
FIG. 10. Effect of FGF-13 treatment on human dermal endothelial cell proliferation . . . (Key: ■=bFGF; ♦FGF-13).

Human lung fibroblasts were cultured with FGF-2 or FGF-13 for 3 days in basal medium before the addition of Alamar Blue to assess effects on growth of the fibroblasts. FGF-2 showed stimulation at 10–2500 ng/ml while FGF-13 showed stimulation at 1000–2500 ng/ml (FIG. 9). However, the maximal effect was similar. In contrast to FGF-2, FGF-13 did not have any stimulatory effect on dermal endothelial cells (FIG. 10).

Figure 11:
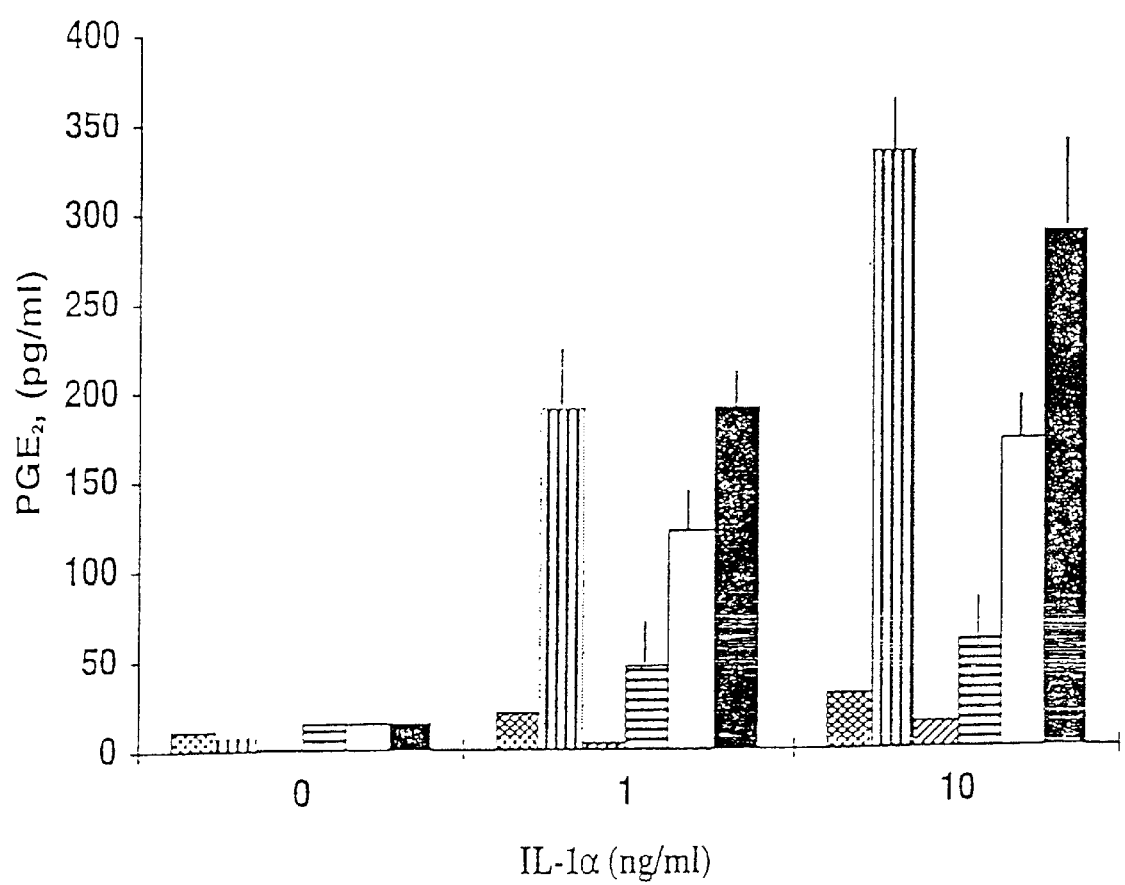
FIG. 11. Effect of FGF-2 and FGF-13 on release of PGE$_2$ from human lung fibroblasts. (Key: in each group of six bars, from left to right the bars represent: medium alone; bFGF (FGF-2) (100 ng.ml); indomethicin (100 ng/ml); FGF-13 (100 ng/ml); FGF-13 (1000 ng/ml); FGF-12 (2500 ng/ml)).
Figure 12:
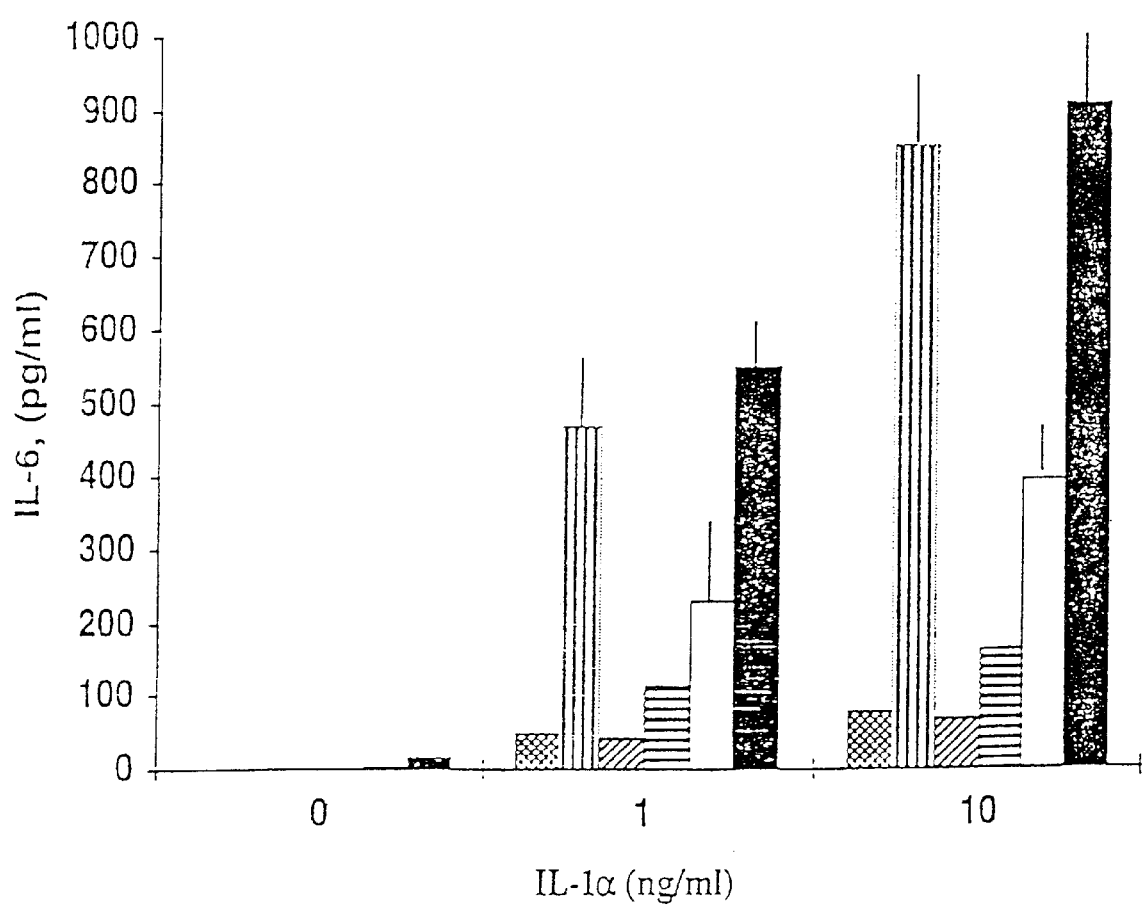
FIG. 12. Effects of FGF-2 and FGF-13 on release of IL-6 from human lung fibroblasts. (Key: in each group of six bars, from left to right the bars represent: medium alone; bFGF (FGF-2) (100 ng.ml); indomethicin (100 ng/ml); FGF-13 (100 ng/ml); FGF-13 (1000 ng/ml); FGF-12 (2500 ng/ml)).

FGF-2 and FGF-13 did not have any effect on $PGE_2$ and IL-6 release from the fibroblasts. IL-1α showed stimulation of $PGE_2$ and IL-6. Both FGF-2 and FGF-13 acted synergistically with IL-1α to release $PGE_2$ (FIG. 11) and IL-6 (FIG. 12). FGF-13 at 2,500 ng/ml gave a similar effects as 100 ng/ml FGF-2. Indomethacin at 100 ng/ml inhibited $PGE_2$ release but not IL-6 release from the fibroblasts.

Angiogenesis Assays

In vivo angiogenesis assay of FGF-13 measures the ability of an existing capillary network to form new vessels in an implanted capsule of murine extracellular matrix material (Matrigel). The protein is mixed with the liquid Matrigel at 4° C. and the mixture is then injected subcutaneously in mice where it solidifies. After 7 days, the solid "plug" of Matrigel is removed and examined for the presence of new blood vessels. Matrigel was purchased from Becton Dickinson Labware/Collaborative Biomedical Products.

When thawed at 4° C. the Matrigel material is a liquid. The Matrigel was mixed with FGF-13 at 150 ng/ml at 4° C. and drawn into cold 3 ml syringes. Female C57B1/6 mice approximately 8 weeks old were injected with the mixture of Matrigel and experimental protein at 2 sites at the midventral aspect of the abdomen (0.5 ml/site). After 7 days, the mice were sacrificed by cervical dislocation, the Matrigel plugs were removed and cleaned (i.e., all clinging membranes and fibrous tissue is removed). Replicate whole plugs were fixed in neutral buffered 10% formaldehyde, embedded in paraffin and used to produce sections for histological examination after staining with Masson's Trichrome. Cross sections from 3 different regions of each plug were processed. Selected sections were stained for the presence of vWF. The positive control for this assay was bovine basic FGF. (150 ng/ml). Matrigel alone was used to determine basal levels of angiogenesis.

FGF-13 was weakly positive in that a small number of infiltrating of cells were observed at the peripheral edge of the Matrigel plug. Immunostaining with antibody to vWF did not reveal vWF-positive endothelial cells. Protocols such as the above which are known in the art generally quantify angiogenesis only by determining the total cellularity of the plug, a procedure which may not give a complete assessment of angiogenic activity of the protein.

Parkinson's Model

The observed loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine. (MPTP). In the CNS, MPTP is taken-up by astrocytes and catabolized by monoamine oxidase B to 1-methyl-4-phenyl pyridine (MPP+) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Figure 14:
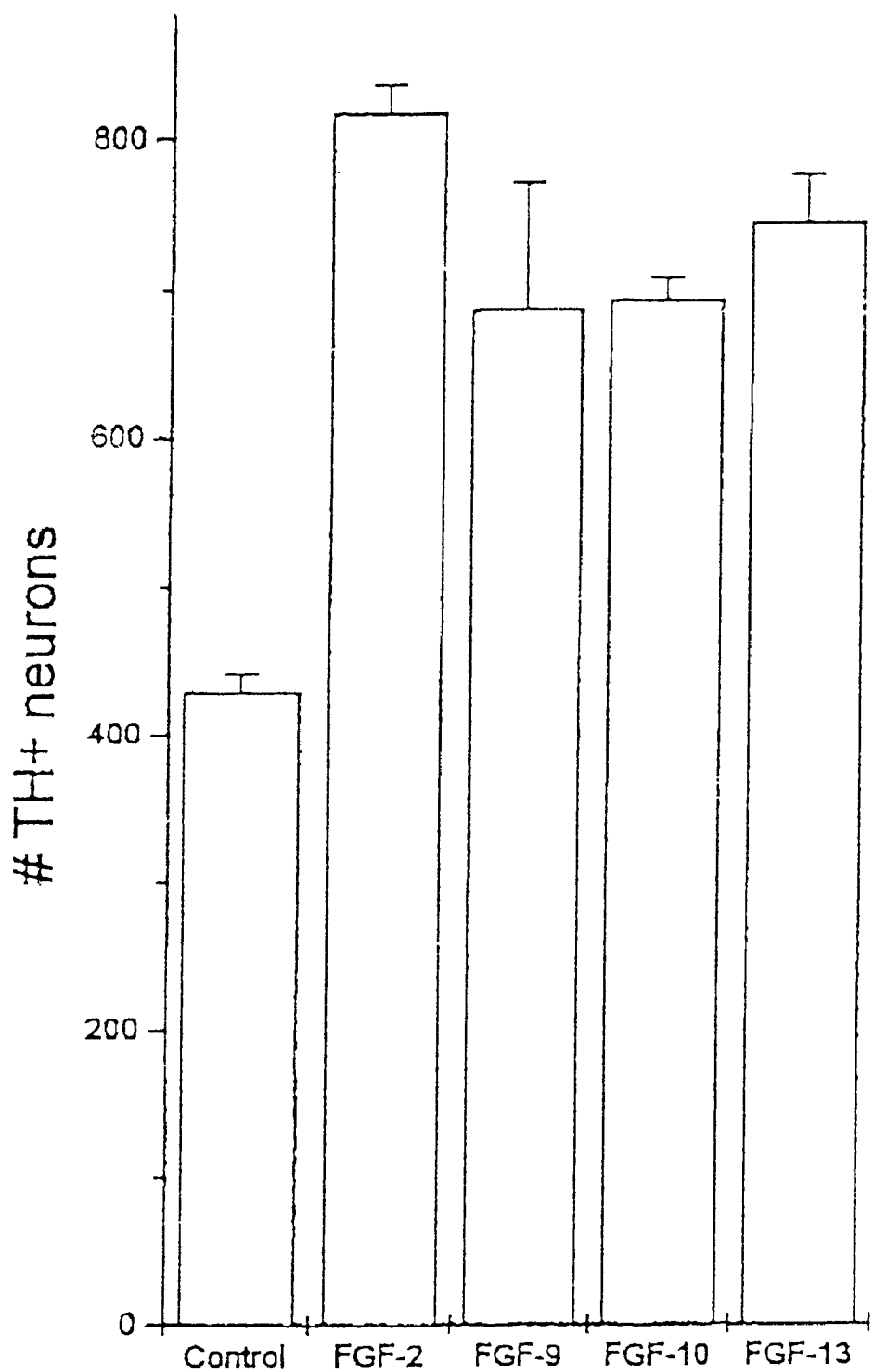
FIG. 14 shows the tyrosine hydroxylase stimulatory activity of FGF13 on cultured dopaminergic neurons from the midbrain floor dissected from E14 Wistar rat embryos, dissociated with trypsin and seeded at a density of 200,000 cells per square centimeter. Tyrosine hydroxylase positive neurons increased after FGF-13 administration. The control was basic FGF, other fibroblase growth factors include FGF-2, FGF-9, and FGF-10.

Based on the data with FGF-2, FGF-13 was evaluated to determine whether it has an action similar to that of FGF-2 in enhancing dopaminergic neuronal survival in vitro and it was then be tested in vivo for protection of dopaminergic neurons in the striatum from the damage associated with MPTP treatment. The potential effect of FGF-13 was first examined in vitro in a dopaminergic neuronal cell culture paradigm. The cultures were prepared by dissecting the midbrain floor plate from gestation day 14 Wistar rat embryos. The tissue was dissociated with trypsin and seeded at a density of 200,000 cells/cm$^2$ on polyorthinine-laminin coated glass coverslips. The cells were maintained in Dulbecco's Modified Eagle's medium and F12 medium containing hormonal supplements (N1). The cultures were fixed with paraformaldehyde after 8 days in vitro and were processed for tyrosine hydroxylase, a specific marker for dopaminergic neurons, immunohistochemical staining. FIG. 14. FGF-13 Increases the Number of Tyrosine Hydroxylase Immunopositive Neurons. Dissociated cell cultures were prepared from embryonic rats. The culture medium was changed every third day and the factors were also added at that time.

Parkinson's Conclusion

Since the dopaminergic neurons were isolated from animals at gestation day 14, a developmental time which is past the stage when the dopaminergic precursor cells are proliferating, the increase in the number of tyrosine hydroxylase immunopositive neurons represents an increase in the number of dopaminergic neurons surviving in vitro. Therefore, FGF-13 acts to prolong the survival of dopaminergic neurons which is needed in Parkinson's Disease.

FGF-13 Biological Activity Conclusions

FGF-13 increases the number of cells, neurite outgrowth, and the level of neuronal specific high-affinity GABA-uptake in cortical cultures derived from embryos at gestation day 16. The results from proliferation assays using purified hippocampal astrocytes demonstrate that FGF-13 increases the amount of [$^3$H]-thymidine incorporation in astrocyte cultures. Although the cortical cell cultures are maintained in serum-free medium in order to inhibit non-neuronal cell proliferation, increases in the number of astrocytes were noted following FGF-2 and FGF-13 treatments. Thus, a portion of the increase in the number of cells observed following FGF-13 treatment is due to the proliferation of astrocytes. However, the robust increase in the neuronal marker (GABA-uptake) suggests that a direct neuronal response is also occurring.

FGF-13 acted similarly to FGF-2 in human lung fibroblasts to stimulate proliferation. Neither had any effect on IL-6 and $PGE_2$ release from fibroblasts but both acted synergisticly with IL-1α. In contrast to FGF-2, however, FGF-13 did not stimulate proliferation in the dermal microvascular endothelial cells. Dopaminergic neuron survival was increased by FGF-13 administration indicating it may have thereapeutic benefits in Parkinson's Disease.

Example 6

Expression and Purification of FGF-13 in *E. coli*

The bacterial expression vector pHE-4 or pHE-4-5 is used for bacterial expression in this example. pHE-4 encodes kanamycin antibiotic resistance ("Kan") and contains a bacterial origin of replication ("ori"), an IPTG inducible promoter, a ribosome binding site ("RBS"), and suitable single restriction enzyme cleavage sites. These elements are arranged such that a DNA fragment encoding a polypeptide may be inserted in such a way as to produce that polypeptide corresponding to the DNA fragment.

The novel pHE4 series of bacterial expression vectors, in particular, the pHE4-5 vector may be used for bacterial expression in this example. (QIAGEN, Inc., 9259 Eton Avenue, Chatsworth, Calif., 91311). The expression plasmid pHE4-5/MPIFΔ23 vector plasmid DNA contains an insert which encodes another ORF. The construct was deposited with the American Type Culture Collection, 10801 University Boulevard, Manassas, Va. 20110-2209, on Sep. 30, 1997 and given Accession No. 209311. Using the Nde I and Asp 718 restriction sites flanking the irrelevant MPIF ORF insert, one of ordinary skill in the art could easily use current molecular biological techniques to replace the irrelevant ORF in the pHE4-5 vector with the FGF-13 ORF of the present invention.

The pHE4-5 bacterial expression vector includes a neomycin phosphotransferase gene for selection, an *E. coli* origin of replication, a T5 phage promoter sequence, two lac operator sequences, a Shine-Delgarno sequence, and the lactose operon repressor gene (lacIq). These elements are arranged such that an inserted DNA fragment encoding a polypeptide expresses that polypeptide with the six His residues (i.e., a "6×His tag") covalently linked to the amino terminus of that polypeptide. The promoter and operator sequences of the pHE4-5 vector were made synthetically. Synthetic production of nucleic acid sequences is well known in the art (CLONETECH 95/96 Catalog, pages 215–216, CLONETECH, 1020 East Meadow Circle, Palo Alto, Calif. 94303).

The DNA sequence encoding the desired portion of the mature FGF-13 protein (i.e., amino acids 20–193 of SEQ ID NO:2) was amplified from the deposited cDNA clone using PCR oligonucleotide primers which anneal to the amino terminal sequences encoding the desired portion of the FGF-13 protein and to sequences in the deposited construct 3' to the cDNA coding sequence. Additional nucleotides containing restrictions sites to facilitate cloning in the pHE-4 vector were added to the 5' and 3' sequences respectively.

A. For cloning the delta 42 form of FGF-13 protein, the 5' primer had the sequence 5' GGG AAT TC<u>C ATA TGA</u> CCG ACC AGC TGA GCA GG (SEQ ID NO:19) containing the underlined Nde I restriction site, which includes an initiation codon and following the initiation codon, 19 nucleotides of the amino terminal coding sequence of the FGF-13 sequence in SEQ ID NO:2. One of ordinary skill in the art would appreciate, of course, that the point in the protein coding sequence where the 5' primer begins may be varied to amplify a desired portion of the complete protein shorter or longer than the mature form. The 3' primer had the sequence GCCCGG <u>GGTACC</u>TTACGTGAGGGGCTGGGGCCG (SEQ ID NO:20 containing the underlined ASP 718 restriction site followed by a stop codon and 18 nucleotides complementary to the 3' end of the coding sequence in the FGF-13 DNA sequence in SEQ ID NO:1.

B. For cloning the 3" delta 9 form of FGF-13 protein, the 5' primer had the sequence 5' GGGAATTC<u>CATATG</u>CAGGGGGAGAATCACCCGTCT 3' (SEQ ID NO:21) containing the underlined Nde I restriction site, which includes an initiation codon and following the initiation codon, 18 nucleotides of the amino terminal coding sequence of the FGF-13 sequence in SEQ ID NO:2. One of ordinary skill in the art would appreciate, of course, that the point in the protein coding sequence where the 5' primer begins may be varied to amplify a desired portion of the complete protein shorter or longer than the mature form. The 3' primer had the sequence GCCCGG<u>GGTACC</u>TTACTTGGTCCGACGGGTGGG (SEQ ID NO:22) containing the underlined ASP 718 restriction site followed by a stop codon and 18 nucleotides complementary to the 3' end of the coding sequence in the FGF-13 DNA sequence in SEQ ID NO:1.

C. In the mature form of FGF-13, there exists a codon coding for a methione at amino acid position 20 according the SEQ ID NO:2. Upstream of this ATG is a nucleotide sequence that may promote ribosome binding in *E. coli* (Shine-Delgarno sequence). To prevent alternate ATG usage in *E. coli*, this sequence was mutated using a 5' primer of the sequence GGGAATTC<u>CATATG</u>CA GGGGGAGAATCACCCGTCTCCTAATTTTA ACCAGTACGTGCGTGACCAGGGCGCCATG (SEQ ID NO 23) containing the underlined Nde I restriction site which includes an initiation codon and following the initiation codon 60 nucleotides of the amino terminal coding sequence of the FGF-13 sequence is SEQ ID NO:2. The 3' primer has the sequence of either SEQ ID NO:20 or SEQ ID NO:22.

The amplified FGF-13 DNA fragments and the vector pHE-4 were digested with Nde I and ASP 718 and the digested DNAs were then ligated together. Insertion of the FGF-13 DNA into the restricted pHE-4 vector places the FGF-13 protein coding region including its associated stop codon downstream from the IPTG-inducible promoter and in-frame with the initiating AUG in the 5' primer.

The ligation mixture was transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain DH5α was used in carrying out the illustrative example described herein. This strain, which is only one of many that are suitable for expressing FGF-13 protein, is available commercially from Life Technologies, Inc., Rockville, Md. Transformants were identified by their ability to grow on LB plates in the presence of kanamycin. Plasmid DNA was isolated from resistant colonies and the identity of the cloned DNA confirmed by restriction analysis, PCR and DNA screening.

Clones containing the desired constructs were grown overnight ("O/N") in liquid culture in LB media supplemented with kanamycin (25 μg/ml). The O/N culture was used to inoculate a large culture, at a dilution of approximately 1:25 to 1:250. The cells are grown to an optical density at 600 nm ("OD$^{600}$") of between 0.4 and 0.6. Isopropyl-b-d-thiogalactopyranoside ("IPTG") is then added to a final concentration of 1 mM to induce transcription from the lac repressor sensitive promoter, by inactivating the lacI repressor. Cells subsequently were incubated further for 3 to 4 hours and were then harvested by centrifugation.

Example 7

Terminal Deletion Variants of FGF-13

Amino and/or Carboxy terminal deletion variants of FGF-13 may be prepared using the primers disclosed in A–D to produce the variants described below. The restriction enzyme sites created are indicated. These variants may be produced using the expression systems disclosed in Example 6.

A. Deletion Variant 1 (FGF13 primers & construct seqs) 5' delta 42/3' delta 9

5' Nde I delta 42 ggg aat tcc ata tga ccg acc agc tga gca gg (SEQ ID NO 24)

3' delta 9 Asp 718 (6335) gcc cgg ggt acc tta ctt ggt ccg acg ggt ggg (SEQ ID NO 25)

ATGACCGACCAGCTGAGCAGGCGGCAGATCCG CGAGTACCAACTCTACAGCAGGACCAGTG GCAAGCACGTGCAGGTCACCGGGCGTCGC ATCTCCGCCACCGCCGAGGACGGCAACA AGTTTGCCAAGCTCATAGTGGAGACGGACA CGTTTGGCAGCCGGGTTCGCATCAAAGGGGCT GAGAGTGAGAAGTACATCTGTATGAACAA GAGGGGCAAGCTCATCGGGAAGCCCAGCGG GAAGAGCAAAGACTGCGTGTTCACGGAGA TCGTGCTGGAGAACAACTATACGGCCTTCCA GAACGCCCGGCACGAGGGCTGGTTCATGGCCT TCACGCGGCAGGGGCGGCCCCGCCAGGCTTC CCGCAGCCGCCAGAACCAGCGCGAGGCCCA CTTCATCAAGCGCCTCTACCAAGGCCAGCTG CCCTTCCCCAACCACGCCGAGAAGCAGAA GCAGTTCGAGTTTGTGGGCTCCGCCCCCA CCCGTCGGACCAAGTAA (SEQ ID NO 26)

MTDQLSRRQIREYQLYSRTSGKHVQVTGRRISA TAEDGNKFAKLIVETDTFGSRVRIKGAESEKYIC MNKRGKLIGKPSGKSKDCVFTEIVLENNYT AFQNARHEGWFMAFTRQGRPRQASRSRQN QREAHFIKRLYQGQLPFPNHAEKQKQFEFVGSA PTRRTK. (SEQ ID NO 27)

B. Deletion Variant 2 (5' delta 42/3' full)

5' Nde I delta 42 ggg aat tcc ata tga ccg acc agc tga gca gg (SEQ ID NO 28)

3' full Asp 718 (6638) gcc cgg ggt acc tta cgt gag ggg ctg ggg ccg (SEQ ID NO 29)

ATGACCGACCAGCTGAGCAGGCGGCAGATCCG CGAGTACCAACTYTACAGCAGGACCAGTGG CAAGCACGTGCAGGTCACCGGGCGTCG CATCTCCGCCACCGCCGAGGACGGCAA CAAGTTTGCCAAGCTCATAGTGGAGACG GACACGTTTGGCAGCCGGGTTCGCATCAA AGGGGCTGAGAGTGAGAAGTACATCTGT ATGAACAAGAGGGGCAAGCTCATCGGGAA GCCCAGCGGGAAGAGCAAAGACTGCGT GTTCACGGAGATCGTGCTGGAGAACAAC TATACGGCCTTCCAGAACGCCCGGCACGA GGGCTGGTTCATGGCCTTCACGCGGCAGGG GCGGCCCCGCCAGGCTTCCCGCAGCCGCCA GAACCAGCGCGAGGCCCACTTCATCAAGC GCCTCTACCAAGGCCAGCTGCCCTTCCCCA ACCACGCCGAGAAGCAGAAGCAGTTCG AGTTTGTGGGCTCCGCCCCCACCCGYCGG ACCAAGCGCACACGGCGGCCCCAGCCCCT CACGTAA (SEQ ID NO 30)

MTDQLSRRQIREYQLYSRTSGKHVQVTGRRI SATAEDGNKFAKLIVETDTFGSRVRIKGAESEKY ICMNKRGKLIGKPSGKSKDCVFTEIVLENNYTAF QNARHEGWFMAFTRQGRPRQASRSRQNQREAH FIKRLYQGQLPFPNHAEKQKQFEFVGSAPTR RTKRTRRPQPLT. (SEQ ID NO 31)

C. Deletion Variant 3 (5' delta23/3' full)

5' NdeI Delta 23 SDG (6881) deletion ggg aat tcc ata tgc agg ggg aga atc acc cgt ctc cta att tta acc agt acg tgc gtg acc agg gcg cca tg (SEQ ID NO 32)

3' delta 9 Asp 718 (6335) gcc cgg ggt acc tta ctt ggt ccg acg ggt ggg (SEQ ID NO 33)

ATGCAGGGGGAGAATCACCCGTCTCCTAATT TTAACCAGTACGTGCGTGACCAGGGCGCCAT GACCGACCAGCTGAGCAGGCGGCAGATCCGC GAGTACCAACTCTACAGCAGGACCAGTGGCA AGCACGTGCAGGTCACCGGGCGTCGCATC TCCGCCACCGCCGAGGACGGCAACAAGTTTGC CAAGCTCATAGTGGAGACGGACACGTTTGG CAGCCGGGTTCGCATCAAAGGGGCTGAGA GTGAGAAGTACATCTGTATGAACAAGAGGGG CAAGCTCATCGGGAAGCCCAGCGGGAAGAG CAAAGACTGCGTGTTCACGGAGATCGTGCTG GAGAACAACTATACGGCCTTCCAGAACGCC CGGCACGAGGGCTGGTTCATGGCCTTCACGCG GCAGGGGCGGCCCCGCCAGGCTTCCCGCAGC CGCCAGAACCAGCGCGAGGCCCACTTCATC AAGCGCCTCTACCAAGGCCAGCTGCCCTTCCCC AACCACGCCGAGAAGCAGAAGCAGTTCGAGTT TGTGGGCTCCGCCCCCACCCGTCGGACCAA GTAA (SEQ ID NO 34)

MQGENHPSPNFNQYVRDQGAMTDQLSRRQIREY QLYSRTSGKHVQVTGRRISATAEDGNKFAKLIVET DTFGSRVRIKGAESEKYICMNKRGKLIGKPSGK SKDCVFTEIVLENNYTAFQNARHEGWFMAFT RQGRPRQASRSRQNQREAHFIKRLYQGQLPFPNH AEKQKQFEFVGSAPTRRTK. (SEQ ID NO 35)

D. Deletion Variant 4 (5' delta 23 SDG deletion/3' full)

5' NdeI Delta 23 SDG (6881) deletion GGG AAT TCC ATA TGC AGG GGG AGA ATC ACC CGT CTC CTA ATT TTA ACC AGT ACG TGC GTG ACC AGG GCG CCA TG (SEQ ID NO 36) 3' FULL ASP 718 (6638) GCC CGG GGT ACC TTA CGT GAG GGG CTG GGG CCG (SEQ ID NO 37)

It will be clear that the invention may be practiced otherwise than as particularly described in the foregoing description and examples. Numerous modifications and variations of the present invention are possible in light of the above teachings and, therefore, are within the scope of the appended claims. The entire disclosure of all publications (including patents, patent applications, journal articles, laboratory manuals, books, or other documents) cited herein are hereby incorporated by reference.

What is claimed is:

1. An isolated protein molecule comprising an amino acid sequence selected from the group consisting of:
   (a) amino acids +1 to +193 of SEQ ID NO:2;
   (b) a mature portion of the protein encoded by the cDNA contained in ATCC Deposit No. 97148;
   (c) amino acids −23 to +193 of SEQ ID NO:2; and
   (d) the full length amino acid sequence encoded by the cDNA contained in ATCC Deposit No. 97148.

2. The isolated protein molecule of claim 1, wherein said amino acid sequence is (a).

3. An isolated protein molecule produced by the method comprising:
   (a) expressing the protein molecule of claim 2 from a host cell; and
   (b) recovering said protein molecule.

4. The isolated protein molecule of claim 1, wherein said amino acid sequence is (b).

5. An isolated protein molecule produced by the method comprising:
   (a) expressing the protein molecule of claim 4 from a host cell; and
   (b) recovering said protein molecule.

6. The isolated protein molecule of claim 1, wherein said amino acid sequence is (c).

7. An isolated protein molecule produced by the method comprising:
   (a) expressing the protein molecule of claim 6 from a host cell; and
   (b) recovering said protein molecule.

8. The isolated protein molecule of claim 1, wherein said amino acid sequence is (d).

9. An isolated protein molecule produced by the method comprising:
   (a) expressing the protein molecule of claim 8 from a host cell; and
   (b) recovering said protein molecule.

10. The isolated protein molecule of claim 1 further comprising a heterologous polypeptide.

11. A composition comprising the protein molecule of claim 1 and a pharmaceutically acceptable carrier.

12. An isolated protein molecule comprising an amino acid sequence selected from the group consisting of:
   (a) at least 30 contiguous amino acids as set forth in SEQ ID NO:2 or encoded by the human cDNA contained in ATCC Deposit No. 97148;
   (b) a polypeptide fragment of the amino acid sequence of SEQ ID NO:2 or a polypeptide fragment encoded by the human cDNA contained in ATCC Deposit No. 97148, wherein said fragment has neural cell activity;
   (c) amino acids +91 to +108 of SEQ ID NO:2; and
   (d) amino acids −22 to +108 of SEQ ID NO:2.

13. The isolated protein molecule of claim 12, wherein said amino acid sequence is (a).

14. The isolated protein molecule of claim 13, wherein said amino acid sequence is at least 50 contiguous amino acids as set forth in SEQ ID NO:2 or encoded by the human cDNA contained in ATCC Deposit No. 97148.

15. An isolated protein molecule produced by the method comprising:
   (a) expressing the protein molecule of claim 13 from a host cell; and
   (b) recovering said protein molecule.

16. The isolated protein molecule of claim 12, wherein said amino acid sequence is (b).

17. An isolated protein molecule produced by the method comprising:
   (a) expressing the protein molecule of claim 16 from a host cell; and
   (b) recovering said protein molecule.

18. The isolated protein molecule of claim 12, wherein said amino acid sequence is (c).

19. An isolated protein molecule produced by the method comprising:
   (a) expressing the protein molecule of claim 18 from a host cell; and
   (b) recovering said protein molecule.

20. The isolated protein molecule of claim 12, wherein said amino acid sequence is (d).

21. An isolated protein molecule produced by the method comprising:
   (a) expressing the protein molecule of claim 20 from a host cell; and
   (b) recovering said protein molecule.

22. The isolated protein molecule of claim 12 further comprising a heterologous polypeptide.

23. A composition comprising the protein molecule of claim 12 and a pharmaceutically acceptable carrier.

24. An isolated protein molecule comprising an amino acid sequence selected from the group consisting of:
   (a) amino acids residues n to +193 of SEQ ID NO:2, wherein n is an integer in the range of −23 to +10;
   (b) amino acids residues −22 to m of SEQ ID NO:2, wherein m is an integer in the range of +154 to +192;
   (c) amino acids n to m of SEQ ID NO:2, wherein n is an integer in the range of −23 to +10 and m is an integer in the range of +154 to +192; and
   (d) a polypeptide consisting of a portion of the complete amino acid sequence encoded by the cDNA clone contained in ATCC Deposit No. 97148 wherein said portion excludes up to 33 amino acids from the amino terminus and up to 39 amino acids from the C-terminus of said complete amino acid sequence.

25. The isolated protein molecule of claim 24, wherein said amino acid sequence is (a).

26. The isolated protein molecule of claim 24, wherein said amino acid sequence is (b).

27. The isolated protein molecule of claim 24, wherein said amino acid sequence is (c).

28. The isolated protein molecule of claim 24, wherein said amino acid sequence is (d).

29. An isolated protein molecule produced by the method comprising:
   (a) expressing the protein molecule of claim 24 from a host cell; and
   (b) recovering said protein molecule.

30. The isolated protein molecule of claim 24 further comprising a heterologous polypeptide.

31. A composition comprising the protein molecule of claim 24 and a pharmaceutically acceptable carrier.

32. An isolated protein molecule comprising a first amino acid sequence having a least 95% identity to a second amino acid sequence selected from the group consisting of:
   (a) amino acids +1 to +193 of SEQ ID NO:2;
   (b) a mature portion of the protein encoded by the cDNA contained in ATCC Deposit No. 97148;
   (c) amino acids −23 to +193 of SEQ ID NO:2; and
   (d) the full length amino acid sequence encoded by the cDNA contained in ATCC Deposit No. 97148,
   wherein % identity is determined using the Bestfit program with parameters that calculate % identity over the full length of said second amino acid sequence and that allow for gaps of homology of up to 5% of the total number of amino acid residues in said second amino acid sequence.

33. The isolated protein molecule of claim 32, wherein said second amino acid sequence is (a).

34. An isolated protein molecule produced by the method comprising:
   (a) expressing the protein molecule of claim 33 from a host cell; and
   (b) recovering said protein molecule.

35. The isolated protein molecule of claim 32, wherein said second amino acid sequence is (b).

36. An isolated protein molecule produced by the method comprising:
   (a) expressing the protein molecule of claim 35 from a host cell; and
   (b) recovering said protein molecule.

37. The isolated protein molecule of claim 32, wherein said second amino acid sequence is (c).

38. An isolated protein molecule produced by the method comprising:
   (a) expressing the protein molecule of claim 37 from a host cell; and
   (b) recovering said protein molecule.

39. The isolated protein molecule of claim 32, wherein said second amino acid sequence is (d).

40. An isolated protein molecule produced by the method comprising:
   (a) expressing the protein molecule of claim 39 from a host cell; and
   (b) recovering said protein molecule.

41. The isolated protein molecule of claim 32 further comprising a heterologous polypeptide.

42. A composition comprising the protein molecule of claim 32 and a pharmaceutically acceptable carrier.

43. An isolated protein molecule comprising a first amino acid sequence having at least 95% identity to a second amino acid sequence selected from the group consisting of:
   (a) amino acids residues n to +193 of SEQ ID NO:2, wherein n is an integer in the range of −23 to +10;
   (b) amino acids residues −22 to m of SEQ ID NO:2, wherein m is an integer in the range of +154 to +192;
   (c) amino acids n to m of SEQ ID NO:2, wherein n is an integer in the range of −23 to +10 and m is an integer in the range of +154 to +192; and
   (d) a polypeptide consisting of a portion of the complete amino acid sequence encoded by the cDNA clone contained in ATCC Deposit No. 97148 wherein said portion excludes up to 33 amino acids from the amino terminus and up to 39 amino acids from the C-terminus of said complete amino acid sequence,
   wherein % identity is determined using the Bestfit program with parameters that calculate % identity over the full length of said second amino acid sequence and that allow for gaps in homology of up to 5% of the total number of amino acids residues in said second amino acid sequence.

44. The isolated protein molecule of claim 43, wherein said amino acid sequence is (a).

45. The isolated protein molecule of claim 43, wherein said amino acid sequence is (b).

46. The isolated protein molecule of claim 43, wherein said amino acid sequence is (c).

47. The isolated protein molecule of claim 43, wherein said amino acid sequence is (d).

48. An isolated protein molecule produced by the method comprising:
   (a) expressing the protein molecule of claim 43 from a host cell; and
   (b) recovering said protein molecule.

49. The isolated protein molecule of claim 43 further comprising a heterologous polypeptide.

50. A composition comprising the protein molecule of claim 43 and a pharmaceutically acceptable carrier.

* * * * *

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 1209 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..648

(ix) FEATURE:
      (A) NAME/KEY: mat_peptide
      (B) LOCATION: 70..648

(ix) FEATURE:
      (A) NAME/KEY: sig_peptide
      (B) LOCATION: 1..67

(xi) SEQUENCE DESCRIPTION: SEQ ID NO: 1:

```
ATG GGA GCC GCC CGC CTG CTG CCC AAC CTC ACT CTG TGC TTA CAG CTG        48
Met Gly Ala Ala Arg Leu Leu Pro Asn Leu Thr Leu Cys Leu Gln Leu
-23         -20                 -15                 -10

CTG ATT CTC TGC TGT CAA ACT CAG GGG GAG AAT CAC CCG TCT CCT AAT        96
Leu Ile Leu Cys Cys Gln Thr Gln Gly Glu Asn His Pro Ser Pro Asn
        -5              -1   1                   5

TTT AAC CAG TAC GTG AGG GAC CAG GGC GCC ATG ACC GAC CAG CTG AGC       144
Phe Asn Gln Tyr Val Arg Asp Gln Gly Ala Met Thr Asp Gln Leu Ser
 10                  15                  20                  25

AGG CGG CAG ATC CGC GAG TAC CAA CTC TAC AGC AGG ACC AGT GGC AAG       192
Arg Arg Gln Ile Arg Glu Tyr Gln Leu Tyr Ser Arg Thr Ser Gly Lys
                 30                  35                  40

CAC GTG CAG GTC ACC GGG CGT CGC ATC TCC GCC ACC GCC GAG GAC GGC       240
His Val Gln Val Thr Gly Arg Arg Ile Ser Ala Thr Ala Glu Asp Gly
             45                  50                  55

AAC AAG TTT GCC AAG CTC ATA GTG GAG ACG GAC ACG TTT GGC AGC CGG       288
Asn Lys Phe Ala Lys Leu Ile Val Glu Thr Asp Thr Phe Gly Ser Arg
         60                  65                  70

GTT CGC ATC AAA GGG GCT GAG AGT GAG AAG TAC ATC TGT ATG AAC AAG       336
Val Arg Ile Lys Gly Ala Glu Ser Glu Lys Tyr Ile Cys Met Asn Lys
     75                  80                  85

AGG GGC AAG CTC ATC GGG AAG CCC AGC GGG AAG AGC AAA GAC TGC GTG       384
Arg Gly Lys Leu Ile Gly Lys Pro Ser Gly Lys Ser Lys Asp Cys Val
 90                  95                 100                 105

TTC ACG GAG ATC GTG CTG GAG AAC AAC TAT ACG GCC TTC CAG AAC GCC       432
Phe Thr Glu Ile Val Leu Glu Asn Asn Tyr Thr Ala Phe Gln Asn Ala
                110                 115                 120

CGG CAC GAG GGC TGG TTC ATG GCC TTC ACG CGG CAG GGG CGG CCC CGC       480
Arg His Glu Gly Trp Phe Met Ala Phe Thr Arg Gln Gly Arg Pro Arg
            125                 130                 135

CAG GCT TCC CGC AGC CGC CAG AAC CAG CGC GAG GCC CAC TTC ATC AAG       528
Gln Ala Ser Arg Ser Arg Gln Asn Gln Arg Glu Ala His Phe Ile Lys
        140                 145                 150

CGC CTC TAC CAA GGC CAG CTG CCC TTC CCC AAC CAC GCC GAG AAG CAG       576
Arg Leu Tyr Gln Gly Gln Leu Pro Phe Pro Asn His Ala Glu Lys Gln
    155                 160                 165
```

-continued

```
AAG CAG TTC GAG TTT GTG GGC TCC GCC CCC ACC CGC GGA ACC AAG CGC    624
Lys Gln Phe Glu Phe Val Gly Ser Ala Pro Thr Arg Arg Thr Lys Arg
170             175                 180                 185

ACA CGG CGG CCC CAG CCC CTC ACG TAGTCTGGGA GGCAGGGGGC AGCAGCCCCT    678
Thr Arg Arg Pro Gln Pro Leu Thr
                190

GGGCCGCCTC CCCACCCCTT TCCCTTCTTA ATCCAAGGAC TGGGCTGGGG TGGCGGGAGG    738

GGAGCCAGAT CCCCGAGGGA GGACCCTGAG GGCCGCGAAG CATCCGAGCC CCCAGCTGGG    798

AAGGGGCAGG CCGGTGCCCC AGGGGCGGCT GGCACAGTGC CCCCTTCCCG GACGGGTGGC    858

AGGCCCTGGA GAGGAACTGA GTGTCACCCT GATCTCAGGC CACCAGCCTC TGCCGGCCTC    918

CCAGCCGGGC TCCTGAAGCC CGCTGAAAGG TCAGCGACTG AAGGCCTTGC AGACAACCGT    978

CTGGAGGTGG CTGTCCTCAA AATCTGCTTC TCGGATCTCC CTCAGTCTGC CCCCAGCCCC   1038

CAAACTCCTC CTGGCTAGAC TGTAGGAAGG GACTTTTGTT TGTTTGTTTG TTTCAGGAAA   1098

AAAGAAAGGG AGAGAGAGGA AAATAGAGGG TTGTCCACTC CTCACATTCC ACGACCCAGG   1158

CCTGCACCCC ACCCCAACT CCCAGCCCCG GAATAAAACC ATTTTCCTGC A             1209
```

(2) INFORMATION FOR SEQ ID NO: 2:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Ala Ala Arg Leu Leu Pro Asn Leu Thr Leu Cys Leu Gln Leu
-23             -20                 -15                 -10

Leu Ile Leu Cys Cys Gln Thr Gln Gly Glu Asn His Pro Ser Pro Asn
            -5              -1  1               5

Phe Asn Gln Tyr Val Arg Asp Gln Gly Ala Met Thr Asp Gln Leu Ser
 10              15                  20                  25

Arg Arg Gln Ile Arg Glu Tyr Gln Leu Tyr Ser Arg Thr Ser Gly Lys
                30                  35                  40

His Val Gln Val Thr Gly Arg Arg Ile Ser Ala Thr Ala Glu Asp Gly
                45                  50                  55

Asn Lys Phe Ala Lys Leu Ile Val Glu Thr Asp Thr Phe Gly Ser Arg
            60                  65                  70

Val Arg Ile Lys Gly Ala Glu Ser Glu Lys Tyr Ile Cys Met Asn Lys
            75                  80                  85

Arg Gly Lys Leu Ile Gly Lys Pro Ser Gly Lys Ser Lys Asp Cys Val
 90              95                  100                 105

Phe Thr Glu Ile Val Leu Glu Asn Asn Tyr Thr Ala Phe Gln Asn Ala
                110                 115                 120

Arg His Glu Gly Trp Phe Met Ala Phe Thr Arg Gln Gly Arg Pro Arg
                125                 130                 135

Gln Ala Ser Arg Ser Arg Gln Asn Gln Arg Glu Ala His Phe Ile Lys
            140                 145                 150

Arg Leu Tyr Gln Gly Gln Leu Pro Phe Pro Asn His Ala Glu Lys Gln
            155                 160                 165

Lys Gln Phe Glu Phe Val Gly Ser Ala Pro Thr Arg Arg Thr Lys Arg
170             175                 180                 185

Thr Arg Arg Pro Gln Pro Leu Thr
```

190

(2) INFORMATION FOR SEQ ID NO: 3:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

(2) INFORMATION FOR SEQ ID NO: 4:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110
```

```
Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

(2) INFORMATION FOR SEQ ID NO: 5:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Gly Leu Ile Trp Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
                20                  25                  30

Gly Gly Val Tyr Glu His Leu Gly Gly Ala Pro Arg Arg Arg Lys Leu
            35                  40                  45

Tyr Cys Ala Thr Lys Tyr His Leu Gln Leu His Pro Ser Gly Arg Val
        50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
            100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Val Ser Ser Thr Pro Gly Ala Arg
130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
            180                 185                 190

Gln Leu Gln Ser Gly Leu Pro Arg Pro Pro Gly Lys Gly Val Gln Pro
        195                 200                 205

Arg Arg Arg Arg Gln Lys Gln Ser Pro Asp Asn Leu Glu Pro Ser His
210                 215                 220

Val Gln Ala Ser Arg Leu Gly Ser Gln Leu Glu Ala Ser Ala His
225                 230                 235

(2) INFORMATION FOR SEQ ID NO: 6:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:
```

```
Met Ser Gly Pro Gly Thr Ala Ala Val Ala Leu Leu Pro Ala Val Leu
 1               5                   10                  15
Leu Ala Leu Leu Ala Pro Trp Ala Gly Arg Gly Gly Ala Ala Ala Pro
             20                  25                  30
Thr Ala Pro Asn Gly Thr Leu Glu Ala Glu Leu Glu Arg Arg Trp Glu
             35                  40                  45
Ser Leu Val Ala Leu Ser Leu Ala Arg Leu Pro Val Ala Ala Gln Pro
         50                  55                  60
Lys Glu Ala Ala Val Gln Ser Gly Ala Gly Asp Tyr Leu Leu Gly Ile
 65                  70                  75                  80
Lys Arg Leu Arg Arg Leu Tyr Cys Asn Val Gly Ile Gly Phe His Leu
                 85                  90                  95
Gln Ala Leu Pro Asp Gly Arg Ile Gly Gly Ala His Ala Asp Thr Arg
                100                 105                 110
Asp Ser Leu Leu Glu Leu Ser Pro Val Glu Arg Gly Val Val Ser Ile
                115                 120                 125
Phe Gly Val Ala Ser Arg Phe Phe Val Ala Met Ser Ser Lys Gly Lys
        130                 135                 140
Leu Tyr Gly Ser Pro Phe Phe Thr Asp Glu Cys Thr Phe Lys Glu Ile
145                 150                 155                 160
Leu Leu Pro Asn Asn Tyr Asn Ala Tyr Glu Ser Tyr Lys Tyr Pro Gly
                165                 170                 175
Met Phe Ile Ala Leu Ser Lys Asn Gly Lys Thr Lys Lys Gly Asn Arg
                180                 185                 190
Val Ser Pro Thr Met Lys Val Thr His Phe Leu Pro Arg Leu
                195                 200                 205

(2) INFORMATION FOR SEQ ID NO: 7:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Met Ser Leu Ser Phe Leu Leu Leu Phe Phe Ser His Leu Ile Leu
 1               5                   10                  15
Ser Ala Trp Ala His Gly Glu Lys Arg Leu Ala Pro Lys Gly Gln Pro
             20                  25                  30
Gly Pro Ala Ala Thr Asp Arg Asn Pro Arg Gly Ser Ser Ser Arg Gln
             35                  40                  45
Ser Ser Ser Ser Ala Met Ser Ser Ser Ala Ser Ser Ser Pro Ala
         50                  55                  60
Ala Ser Leu Gly Ser Gln Gly Ser Gly Leu Glu Gln Ser Ser Phe Gln
 65                  70                  75                  80
Trp Ser Leu Gly Ala Arg Thr Gly Ser Leu Tyr Cys Arg Val Gly Ile
                 85                  90                  95
Gly Phe His Leu Gln Ile Tyr Pro Asp Gly Lys Val Asn Gly Ser His
                100                 105                 110
Glu Ala Asn Met Leu Ser Val Leu Glu Ile Phe Ala Val Ser Gln Gly
                115                 120                 125
Ile Val Gly Ile Arg Gly Val Phe Ser Asn Lys Phe Leu Ala Met Ser
        130                 135                 140
```

```
Lys Lys Gly Lys Leu His Ala Ser Ala Lys Phe Thr Asp Asp Cys Lys
145                 150                 155                 160

Phe Arg Glu Arg Phe Gln Glu Asn Ser Tyr Asn Thr Tyr Ala Ser Ala
            165                 170                 175

Ile His Arg Thr Glu Lys Thr Gly Arg Glu Trp Tyr Val Ala Leu Asn
            180                 185                 190

Lys Arg Gly Lys Ala Lys Arg Gly Cys Ser Pro Arg Val Lys Pro Gln
            195                 200                 205

His Ile Ser Thr His Phe Leu Pro Arg Phe Lys Gln Ser Glu Gln Pro
210                 215                 220

Glu Leu Ser Phe Thr Val Thr Val Pro Glu Lys Lys Asn Pro Pro Ser
225                 230                 235                 240

Pro Ile Lys Ser Lys Ile Pro Leu Ser Ala Pro Arg Lys Asn Thr Asn
                245                 250                 255

Ser Val Lys Tyr Arg Leu Lys Phe Arg Phe Gly
            260                 265

(2) INFORMATION FOR SEQ ID NO: 8:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
                20                  25                  30

Gly Met Val Val Pro Ser Pro Ala Gly Thr Arg Ala Asn Asn Thr Leu
            35                  40                  45

Leu Asp Ser Arg Gly Trp Gly Thr Leu Leu Ser Arg Ser Arg Ala Gly
50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
            115                 120                 125

Ser Leu Phe Gly Val Arg Ser Ala Leu Phe Val Ala Met Asn Ser Lys
130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
            195                 200                 205

(2) INFORMATION FOR SEQ ID NO: 9:
```

(i) SEQUENCE CHARACTERISTICS:
    (A) LENGTH: 194 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 9:

```
Met His Lys Trp Ile Leu Thr Trp Ile Leu Pro Thr Leu Leu Tyr Arg
 1               5                  10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr
```

(2) INFORMATION FOR SEQ ID NO: 10:

(i) SEQUENCE CHARACTERISTICS:
    (A) LENGTH: 215 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 10:

```
Met Gly Ser Pro Arg Ser Ala Leu Ser Cys Leu Leu Leu His Leu Leu
 1               5                  10                  15

Val Leu Cys Leu Gln Ala Gln Val Thr Val Gln Ser Ser Pro Asn Phe
                20                  25                  30

Thr Gln His Val Arg Glu Gln Ser Leu Val Thr Asp Gln Leu Ser Arg
            35                  40                  45

Arg Leu Ile Arg Thr Tyr Gln Leu Tyr Ser Arg Thr Ser Gly Lys His
        50                  55                  60

Val Gln Val Leu Ala Asn Lys Arg Ile Asn Ala Met Ala Glu Asp Gly
 65                  70                  75                  80

Asp Pro Phe Ala Lys Leu Ile Val Glu Thr Asp Thr Phe Gly Ser Arg
                85                  90                  95
```

```
Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
        115                 120                 125

Phe Thr Glu Ile Val Leu Glu Asn Asn Tyr Thr Ala Leu Gln Asn Ala
        130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
        195                 200                 205

Thr Trp Ala Pro Glu Pro Arg
    210                 215
```

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
GCCAGACCAT GGAGAATCAC CCGTCTCCTA AT                                32
```

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
GATTTAAGAT CTCGTGAGGG GCTGGGGCCG                                   30
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
CTAGTCGCAT GCAGGGGGAG AATCACCCGT CT                                32
```

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear

```
    (ii) MOLECULE TYPE: DNA (genomic)

(xi) SEQUENCE DESCRIPTION: SEQ ID NO: 14:

GCTTGAAAGC TTCTACGTGA GGGGCTGGGG CCG                                       33

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CTAGTGGATC CCGAGAATCA CCCGTCTCCT                                           30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CGACTTCTAG AACCTCGGGG ATCTGGCTCC                                           30

(2) INFORMATION FOR SEQ ID NO: 17:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

CTAGCCGGAT CCGCCACCAT GAACTCCTTC TCCACAAGCG CCTTCGGTCC AGTTGCCTTC          60

TCCCTGGGGC TGCTCCTGGT GTTGCCTGCT GCCTTCCCTG CCCCAGTTGT GAGACCAGGG         120

GGAGAATCAC CCGTCT                                                        136

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GCTTGATCTA GACGTGAGGG GCTGGGGCCG                                           30

(2) INFORMATION FOR SEQ ID NO: 19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 19:

GGGAATTCCAT ATGACCGACC AGCTGAGCAG G                                    32

(2) INFORMATION FOR SEQ ID NO: 20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 20:

GCCCGGGGTA CCTTACGTGA GGGGCTGGGG CCG                                   33

(2) INFORMATION FOR SEQ ID NO: 21:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 21:

GGGAATTCCA TATGCAGGGG GAGAATCACC CGTCT                                 35

(2) INFORMATION FOR SEQ ID NO: 22:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 22:

GCCCGGGGTA CCTTACTTGG TCCGACGGGT GGG                                   33

(2) INFORMATION FOR SEQ ID NO: 23:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 23:

GGGAATTCCA TATGCAGGGG GAGAATCACC CGTCTCCTAA TTTTAACCAG TACGTGCGTG      60

ACCAGGGCGC CATG                                                        74

(2) INFORMATION FOR SEQ ID NO: 24:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 24:

GGGAATTCCA TATGACCGAC CAGCTGAGCA GG                                   32

(2) INFORMATION FOR SEQ ID NO: 25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

GCCCGGGGTA CCTTACTTGG TCCGACGGGT GGG                                  33

(2) INFORMATION FOR SEQ ID NO: 26:

(i) SEQUENCE CHARACTERISTICS:
        (A) LENGTH: 497 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

ATGACCGACC AGCTGAGCAG GCGGCAGATC CGCGAGTACC AACTCTACAG CAGGACCAGT     60

GGCAAGCACG TGCAGGTCAC CGGGCGTCGC ATCTCCGCCA CCGCCGAGGA CGGCAACAAG    120

TTTGCCAAGC TCATAGTGGA GACGGACACG TTTGGCAGCC GGGTTCGCAT CAAAGGGGCT    180

GAGAGTGAGA AGTACATCTG TATGAACAAG AGGGGCAAGC TCATCGGGAA GCCCAGCGGG    240

AAGAGCAAAG ACTGCGTGTT CACGGAGATC GTGCTGGAGA ACAACTATAC GGCCTTCCAG    300

AACGCCCGGC ACGAGGGCTG GTTCATGGCC TTCACGCGGC AGGGGCGGCC CCGCCAGGCT    360

TCCCGCAGCC GCCAGAACCA GCGCGAGGCC CACTTCATCA AGCGCTCTAC CAAGGCCAGC    420

TGCCCTTCCC CAACCACGCC GAGAAGCAGA AGCAGTTCGA GTTTGTGGGC TCCGCCCCCA    480

CCCGTCGGAC CAAGTAA                                                    497

(2) INFORMATION FOR SEQ ID NO: 27:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Met Thr Asp Gln Leu Ser Arg Arg Gln Ile Arg Glu Tyr Gln Leu Tyr
1               5                   10                  15

Ser Arg Thr Ser Gly Lys His Val Gln Val Thr Gly Arg Arg Ile Ser
            20                  25                  30

Ala Thr Ala Glu Asp Gly Asn Lys Phe Ala Lys Leu Ile Val Glu Thr
        35                  40                  45

Asp Phe Gly Ser Arg Val Arg Ile Lys Gly Ala Glu Ser Glu Lys Tyr
    50                  55                  60

Ile Cys Met Asn Lys Arg Gly Lys Leu Ile Gly Lys Pro Ser Gly Lys
65                  70                  75                  80

Ser Lys Asp Cys Val Phe Thr Glu Ile Val Leu Glu Asn Asn Tyr Thr

```
            85                  90                  95
Ala Phe Gln Asn Ala Arg His Glu Gly Trp Phe Met Ala Phe Thr Arg
            100                 105                 110
Gln Gly Arg Pro Arg Gln Ala Ser Arg Ser Arg Gln Asn Gln Arg Glu
            115                 120                 125
Ala His Phe Ile Lys Arg Leu Tyr Gln Gly Gln Leu Pro Phe Pro Asn
            130                 135                 140
His Ala Glu Lys Gln Lys Gln Phe Glu Phe Val Gly Ser Ala Pro Thr
145                 150                 155                 160
Arg Arg Thr Lys (2) INFORMATION FOR SEQ ID NO: 28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

GGGAATTCCA TATGACCGAC CAGCTGAGCA GG                              32

(2) INFORMATION FOR SEQ ID NO: 29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GCCCGGGGTA CCTTACGTGA GGGGCTGGGG CCG                             33

(2) INFORMATION FOR SEQ ID NO: 30:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

ATGACCGACC AGCTGAGCAG GCGGCAGATC CGCGAGTACC AACTTACAGC AGGACCAGTG    60

GCAAGCACGT GCAGGTCACC GGGCGTCGCA TCTCCGCCAC CGCCGAGGAC GGCAACAAGT   120

TTGCCAAGCT CATAGTGGAG ACGGACACGT TTGGCAGCCG GGTTCGCATC AAAGGGGCTG   180

AGAGTGAGAA GTACATCTGT ATGAACAAGA GGGGCAAGCT CATCGGGAAG CCCAGCGGGA   240

AGAGCAAAGA CTGCGTGTTC ACGGAGATCG TGCTGGAGAA CAACTATACG GCCTTCCAGA   300

ACGCCCGGCA CGAGGGCTGG TTCATGGCCT TCACGCGGCA GGGGCGGCCC CGCCAGGCT    360

TCCCGCAGCC GCCAGAACCA GCGCGAGGCC CACTTCATCA AGCGCCTCTA CCAAGGCCAG   420

CTGCCCTTCC CCAACCACGC CGAGAAGCAG AAGCAGTTCG AGTTTGTGGG CTCCGCCCCC   480

ACCCGCGGAC CAAGCGCACA CGGCGGCCCC AGCCCCTCAC GTAA                    524

(2) INFORMATION FOR SEQ ID NO: 31:
```

(i) SEQUENCE CHARACTERISTICS:
    (A) LENGTH: 175 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 31:

```
Met Thr Asp Gln Leu Ser Arg Arg Gln Ile Arg Glu Tyr Gln Leu Tyr
1               5                   10                  15

Ser Arg Thr Ser Gly Lys His Val Gln Val Thr Gly Arg Arg Ile Ser
            20                  25                  30

Ala Thr Ala Glu Asp Gly Asn Lys Phe Ala Lys Leu Ile Val Glu Thr
        35                  40                  45

Asp Thr Phe Gly Ser Arg Val Arg Ile Lys Gly Ala Glu Ser Glu Lys
    50                  55                  60

Tyr Ile Cys Met Asn Lys Arg Gly Lys Leu Ile Ile Gly Lys Pro Ser
65                  70                  75                  80

Gly Lys Ser Lys Asp Cys Val Phe Thr Glu Ile Val Leu Glu Asn Asn
            85                  90                  95

Tyr Thr Ala Phe Gln Asn Ala Arg His Glu Gly Trp Phe Met Ala Phe
            100                 105                 110

Thr Arg Gln Gly Arg Pro Arg Gln Ala Ser Arg Ser Arg Gln Asn Gln
            115                 120                 125

Arg Glu Ala His Phe Ile Lys Arg Leu Tyr Gln Gly Gln Leu Pro Phe
130                 135                 140

Pro Asn His Ala Glu Lys Gln Lys Gln Phe Glu Phe Val Gly Ser Ala
145                 150                 155                 160

Pro Thr Arg Arg Thr Lys Arg Thr Arg Arg Pro Gln Pro Leu Thr
                165                 170                 175
```

(2) INFORMATION FOR SEQ ID NO: 32:

(i) SEQUENCE CHARACTERISTICS:
    (A) LENGTH: 74 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 32:

GGGAATTCCA TATGCAGGGG GAGAATCACC CGTCTCCTAA TTTTAACCAG TACGTGCGTG    60

ACCAGGGCGC CATG    74

(2) INFORMATION FOR SEQ ID NO: 33:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 33:

GCCCGGGGTA CCTTACTTGG TCCGACGGGT GGG    33

(2) INFORMATION FOR SEQ ID NO: 34:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
ATGCAGGGGG AGAATCACCC GTCTCCTAAT TTTAACCAGT ACGTGCGTGA CCAGGGCGCC      60

ATGACCGACC AGCTGAGCAG GCGGCAGATC CGCGAGTACC AACTCTACAG CAGGACCAGT     120

GGCAAGCACG TGCAGGTCAC CGGGCGTCGC ATCTCCGCCA CCGCCGAGGA CGGCAACAAG     180

TTTGCCAAGC TCATAGTGGA GACGGACACG TTTGGCAGCC GGGTTCGCAT CAAAGGGCTG     240

AGAGTGAGAA GTACATCTGT ATGAACAAGA GGGGCAAGCT CATCGGGAAG CCCAGCGGGA     300

AGAGCAAAGA CTGCGTGTTC ACGGAGATCG TGCTGGAGAA CAACTATACG GCTTCCAGAA     360

CGCCCGGCAC GAGGGCTGGT TCATGGCCTT CACGGGCAGG GGCGGCCCCG CCAGGCTTCC     420

CGCAGCCGCC AGAACCAGCG CGAGGCCCAC TTCATCAAGC GCCTCTACCA AGGCCAGCTG     480

CCCTTCCCCA ACCACGCCGA GAAGCAGAAG CAGTTCGAGT TTGTGGCTCC GCCCCCACCC     540

GTCGGACCAA GTAA                                                      554
```

(2) INFORMATION FOR SEQ ID NO: 35:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 35:

```
Met Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
    130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys
            180                 185
```

(2) INFORMATION FOR SEQ ID NO: 36:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
GGGAATTCCA TATGCAGGGG GAGAATCACC CGTCTCCTAA TTTTAACCAG TACGTGCGTG    60

ACCAGGGCGC AATG                                                     74
```

(2) INFORMATION FOR SEQ ID NO: 37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

```
GCCCGGGGTA CCTTACGTGA GGGGCTGGGG CCG                                33
```